US007879351B2

(12) United States Patent
Li et al.

(10) Patent No.: US 7,879,351 B2
(45) Date of Patent: *Feb. 1, 2011

(54) HIGH DELIVERY RATES FOR LIPID BASED DRUG FORMULATIONS, AND METHODS OF TREATMENT THEREOF

(75) Inventors: Zhili Li, Kendall Park, NJ (US); Lawrence T. Boni, Monmouth Junction, NJ (US); Brian S. Miller, Mercerville, NJ (US); Vladimir Malinin, Plainsboro, NJ (US); Xingong Li, Cranbury, NJ (US)

(73) Assignee: Transave, Inc., Monmouth Junction, NJ (US)

( * ) Notice: Subject to any disclaimer, the term of this patent is extended or adjusted under 35 U.S.C. 154(b) by 1115 days.

This patent is subject to a terminal disclaimer.

(21) Appl. No.: 11/398,859

(22) Filed: Apr. 6, 2006

(65) Prior Publication Data

US 2007/0077290 A1 Apr. 5, 2007

Related U.S. Application Data

(63) Continuation-in-part of application No. 11/185,448, filed on Jul. 19, 2005, now Pat. No. 7,718,189, which is a continuation-in-part of application No. 11/023,971, filed on Dec. 28, 2004, now abandoned, which is a continuation-in-part of application No. 10/696,389, filed on Oct. 29, 2003, now Pat. No. 7,544,369.

(60) Provisional application No. 60/421,923, filed on Oct. 29, 2002.

(51) Int. Cl.
  *A61K 9/127* (2006.01)
(52) U.S. Cl. .................................................... 424/450
(58) Field of Classification Search .................. 424/450
  See application file for complete search history.

(56) References Cited

U.S. PATENT DOCUMENTS

| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,693,999 A | 9/1987 | Axelsson et al. |

(Continued)

FOREIGN PATENT DOCUMENTS

EP   0069307 A   1/1983

(Continued)

OTHER PUBLICATIONS

Alton et al., "Cationic lipid-mediated CFTR gene transfer to the lungs and nose of patients with cystic fibrosis: a double-blind placebo-controlled trial," The Lancet, 353:947-954 (1999).

(Continued)

*Primary Examiner*—Gollamudi S Kishore
(74) *Attorney, Agent, or Firm*—Foley Hoag LLP

(57) ABSTRACT

Provided is a method of preparing lipid based drug formulations with low lipid/drug ratios using coacervation techniques. Also provided are methods of delivering such lipid based drug formulations at high delivery rates, and methods of treating patients with pulmonary diseases comprising administering such lipid based drug formulations.

18 Claims, 11 Drawing Sheets

SPUTUM/BIOFILM of CF PATIENTS

Epithelial Cells
● SLIT Antibiotic
+ Free aminoglycoside
− Mucin, alginate, DNA
━ *Pseudomonas aeruginosa*

U.S. PATENT DOCUMENTS

| | | |
|---|---|---|
| 4,767,874 A | 8/1988 | Shima et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,023,087 A | 6/1991 | Yau-Young |
| 5,030,453 A | 7/1991 | Lenk et al. |
| 5,049,388 A * | 9/1991 | Knight et al. ............... 424/450 |
| 5,049,389 A | 9/1991 | Radhakrishnan |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,211,955 A | 5/1993 | Legros et al. |
| 5,264,618 A | 11/1993 | Felgner et al. |
| 5,269,979 A | 12/1993 | Fountain |
| 5,279,833 A | 1/1994 | Rose |
| 5,320,906 A | 6/1994 | Eley et al. |
| 5,334,761 A | 8/1994 | Gebeyehu et al. |
| 5,409,704 A | 4/1995 | Bally et al. |
| 5,459,127 A | 10/1995 | Felgner et al. |
| 5,540,936 A | 7/1996 | Coe et al. |
| 5,543,152 A | 8/1996 | Webb et al. |
| 5,569,464 A | 10/1996 | Endo et al. |
| 5,616,334 A | 4/1997 | Janoff et al. |
| 5,641,662 A | 6/1997 | Debs |
| 5,643,599 A | 7/1997 | Lee et al. |
| 5,662,929 A | 9/1997 | Lagace et al. |
| 5,665,383 A | 9/1997 | Grinstaff et al. |
| 5,723,147 A | 3/1998 | Kim et al. |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,795,589 A | 8/1998 | Mayer et al. |
| 5,820,848 A | 10/1998 | Boni et al. |
| 5,843,473 A | 12/1998 | Woodle et al. |
| 5,849,490 A | 12/1998 | Schonwetter et al. |
| 5,875,776 A | 3/1999 | Vaghefi |
| 5,945,122 A | 8/1999 | Abra et al. |
| 6,045,828 A | 4/2000 | Bystrom et al. |
| 6,051,251 A | 4/2000 | Zalipsky et al. |
| 6,086,851 A | 7/2000 | Boni et al. |
| 6,090,407 A | 7/2000 | Knight et al. |
| 6,147,060 A | 11/2000 | Zasloff et al. |
| 6,211,162 B1 | 4/2001 | Dale et al. |
| 6,221,388 B1 | 4/2001 | Hersch et al. |
| 6,352,996 B1 | 3/2002 | Cao et al. |
| 6,419,901 B2 | 7/2002 | Placke et al. |
| 6,440,393 B1 | 8/2002 | Waldrep et al. |
| 6,451,784 B1 | 9/2002 | Placke et al. |
| 6,497,901 B1 | 12/2002 | Royer |
| 6,511,676 B1 | 1/2003 | Boulikas |
| 6,599,912 B1 | 7/2003 | Au et al. |
| 6,843,942 B2 | 1/2005 | Katinger et al. |
| 7,544,369 B2 * | 6/2009 | Boni et al. ............... 424/450 |
| 2001/0006660 A1 | 7/2001 | Lagace et al. |
| 2002/0086852 A1* | 7/2002 | Cantor et al. ............... 514/54 |
| 2002/0187105 A1 | 12/2002 | Zou et al. |
| 2003/0059375 A1 | 3/2003 | Perez-Soler et al. |
| 2003/0118636 A1 | 6/2003 | Friesen et al. |
| 2005/0019926 A1 | 1/2005 | Gonda et al. |

FOREIGN PATENT DOCUMENTS

| | | |
|---|---|---|
| GB | 2145107 A | 3/1985 |
| JP | 10-511363 T | 11/1998 |
| WO | WO-86/06959 | 12/1986 |
| WO | WO-91/16882 | 11/1991 |
| WO | WO-93/12240 | 6/1993 |
| WO | WO-94/12155 | 6/1994 |
| WO | WO-94/12156 | 6/1994 |
| WO | WO-96/19199 | 6/1996 |
| WO | WO-96/19972 | 7/1996 |
| WO | WO-99/65466 | 12/1999 |
| WO | WO-00/27359 | 5/2000 |
| WO | WO-00/29103 | 5/2000 |
| WO | WO-03/075889 | 9/2003 |

OTHER PUBLICATIONS

Poyner et al., "A comparative study on the pulmonary delivery of tobramycin encapsulated into liposomes and PLA microspheres following intravenous and endotracheal delivery," Journal of Controlled Release, 35:41-48 (1995).

Schreier et al., "Pulmonary delivery of liposomes," Journal of Controlled Release, 24:209-233 (1993).

Sermet-Gaudelus et al., "Nebulized Antibiotics in Cystic Fibrosis," Paediatric Drugs, 4(7):455-467 (2002).

Supplementary European Search Report dated Jan. 12, 2009 for 03816990.0

Antos et al., (1995) Antibacterial activity of liposomal amikacin against *Pseudomonas aeruginosa* in vitro. Pharmacological Research 32(1/2): 84-87.

Bakker-Woudenberg et al., (1995) Efficacy of gentamicin or ceftazidine entrapped in liposomes with prolonged blood circulation and enhanced localization in Klebsiella pneumoniae-infected lung tissue. Journal Infectious Diseases 171:938-947.

Bargoni et al., (2001) Transmucosl transport of tobramycin incorporated in solid lipid nanoparticles (SLN) after duodenal administration to rats. Part II—Tissue distribution. Pharmacological Research 43(5): 497-502.

Beaulac et al., (1997) in vitro kinetics of drug release and pulmonary retention of microencapsulated antibiotic in liposomal formulations in relation to the lipid composition. Journal Microencapsulation 14(3): 335-348.

Beaulac et al., (1999) Aerolization of low phase transition temperature liposomal tobramycin as a dry powder in an animal model of chronic pulmonary infection caused by *Pseudomonas aeruginosa*. Journal Drug Targeting 7(1): 33-41.

Bermudez et al., (1999) Treatment of Disseminated Mycobacterium avium Complex Infection of Beige Mice with Liposome-Encapsulated Aminoglycosides. Journal Infect. Dis. 161: 1262-1268.

Bucke et al., (1997) Surface-Modified Amikacin-Liposomes: Organ Distribution and Interaction with Plasma Proteins. Journal Drug Targeting 5(2): 99-108.

Comis, "Carboplatin in the Treatment of Non-Small Cell Lung Cancer: a Review," Oncology, Nov. 1993; 50 (2): 37-41. (Abstract).

Cynamon et al., (1989) Liposome-Encapsulated-Amikacin Therapy of Mycobacterium avium Complex Infection in Geige Mice. Antimicrobial Agents and Chemotherapy 33(8): 1179-1183.

Dees et al., (1990) The mechanism of enhanced intraphagocytic killing of bacteria by liposomes containing antibiotics. Veterinary Immunology and Immunopathology 24: 135-146.

Demaeyer et al., (1993) Disposition of liposomal gentamicin following intrabronchial administration in rabbits. Journal Microencapsulation 10(1): 77-88.

Ehlers et al., (1996) Liposomal amikacin for treatment of M. avium Infections in clinically relevant experimental settings. Zbl. Bakt. 284: 218-231.

Fielding et al., (1999) Pharmacokinetics and Urinary Excretion of Amikacin in Low-Clearance Unilamellar Liposomes after a Single or Repeated Intravenous Administration in the Rhesus Monkey. Antimicrobial Agents and Chemotherapy 43(3): 503-509.

Fountain et al., (1985) Treatment of *Brucella canis* and *Brucella abortus* in vitro and in vivo by stable plurilamellar vesicle-encapsulated aminoglycosides. Journal Infectious Diseases 152(3): 529-535.

Howell, S.B., (2001) Clinical applications of a novel sustained-release injectable drug delivery system: Depofoam Technology. Cancer Journal 7: 219-227.

Katare, O.P., et al., Enhanced in vivo Performance of Liposomal Indomethacin Derived From Effervescent Granule Based Proliposomes, J. Microencapsulation, 1995, vol. 12, No. 5, pp. 487-493.

Kesavalu et al., (1990) Differential effects of free and liposome encapsulated amikacin on the survival of *Mycobacterium avium* complex in mouse peritoneal macrophages. Tubercle 71: 215-218.

Kim et al., (1990) Pharmacokinetics of intravitreally injected liposomes encapsulated tobramycin in normal rabbits. Yonsei Medical Journal 31(4): 308-314.

Klemens et al., (1990) Liposome-encapsulated-gentamicin therapy of *Mycobacterium avium* complex infection in beige mice. Antimicrobial Agents and Chemotherapy 34(6) 967-970.

Lagace et al., (1991) Liposome-encapsulated antibiotics: preparation, drug release and antimicrobial activity against *Pseudomona aeruginosa*. Journal Microencapsulation 8(1): 53-61.

Lutwyche et al., (1998) Intracellular delivery and antibacterial activity of gentamicin encapsulated in pH-sensitive liposomes. Antimicrobial Agents and Chemotherapy 42(10) 2511-2520.

Marier et al., (2003) Liposomal tobramycin against pulmonary infections of *Pseudomonas aeruginosa:* a pharmacokinetic and efficacy study following single and multiple intratracheal administrations in rats. Journal Antimicrobial Chemotherapy 52: 247-252.

Morgan et al., (1980) Preparation and properties of liposome-associated gentamicin. Antimicrobial Agents and Chemotherapy 17(4) 544-548.

Nightingale et al., (1993) Liposome-encapsulated gentamicin treatment of *Mycobacterium avium-Mycobacterium intracellulare* complex bacteremia in AIDS patients. Antimicrobial Agents and Chemotherapy 37(9) 1869-1872.

Niven, Ralph et al., Nebulization of Liposomes. I. Effects of Lipid Composition, Report, pp. 1127-1133.

Omri et al., (1994) Pulmonary retention of free and liposome-encapsulated tobramycin after intratracheal administration in uninfected rats and rats infected with *Pseudomonas aeruginosa.* Antimicrobial Agents and Chemotherapy 38(5) 1090-1095.

Omri et al., (1995) Incorporation, release and in vitro antibacterial activity of liposomal aminoglycosides against *Pseudomonas aeruginosa.* Journal Antimicrobial Chemotherapy 36: 631-639.

Omri et al., (1996) Comparison of the Bactericidal Action of Amikacin, Netilmicin and Tobramtcin in Free and Liposomal Formulation against *Pseudomonas aeruginosa.* Chemotherapy 42: 170-176.

Petersen et al., (1996) Liposomal amikacin: improved treatment of Mycibacterium avium complex infection in the beige mouse model. Journal Antimicrobial Chemotherapy 38: 819-828.

Petkowicz, Jozefa, et al., Hypoglycemic Effect of Liposome-Entrapped Insulin Administered by Various Routes into Normal Rats, Pol. J. Pharmacol. Pharm., 1989, 41, pp. 299-304.

Poyner et al., (1993) Preparation, properties and the effects of free and liposomal tobramycin on siderophore production by *Pseudomonas aeruginosa.* Journal Antimicrobial Chemotherapy 34: 43-52.

Price et al., (1989) Enhanced effectiveness of intraperitoneal antibiotics administered via liposomal carrier. Arch Surgery 124: 1411-1415.

Price et al., (1992) Liposome delivery of aminoglycosides in burn wounds. Surgery, Gynecology &Obstetrics 174: 414-418.

Price et al., (1994) Liposome encapsulation: a method for enhancing the effectiveness of local antibiotics. Surgery, 115(4): 480-4487.

Ramsammy et al., (1988) The effect of gentamicin on the biophysical properties of phosphatidic acid liposomes is influenced by the O-C=O group of the lipid. Biochemistry 27: 8249-8254.

Roehrborn et al., (1995) Lipid-based slow-release formulation of amikacin sulfate reduces foreign body associated infections in mice. Antimicrobial Agents Chemotherapy 39: 1752-1755.

Schiffelers et al., (2001) in vivo synergistic interaction of liposome-coencapsulated gentamicin and ceftazidime. Journal Pharmacology Experimental Therapeutics 298(1): 369-375.

Schiffelers et al., (2001) Therapeutic efficacy of liposomal gentamicin in clinically relevant rat models. International Journal Pharmaceutics 214: 103-105.

Swenson et al., (1990) Pharmacokinetics and in vivo activity of liposome-encapsulated gentamicin. Antimicrobial Agents and Chemotherapy 34(2) 235-240.

Trafny et al., (1995) Effects of free and liposome-encapsulated antibiotics on adherence of *Pseudomonas aeruginosa* to collagen type I. Antimicrobial Agents and Chemotherapy 39(12) 2645-2649.

Vitas et al., (1996) Effect of composition and method of preparation of liposomes on their stability and interaction with murine monocytes infected with Brucella abortus. Antimicrobial Agents and Chemotherapy 40(1) 146-151.

Whitehead et al., (1998) Kinetics and Toxicity of Liposomal and conventional Amikacinin a Patient with a Multidrug-Resistant Tuberculosis. Eur J Clin Microbiol Infect Dis 17: 794-797.

Yanagihara, K. (2002) Design of anti-bacterial drug and anti-Mycobacterial drug for drug delivery system. Current Pharmaceutical Design 8: 475-482.

Zeng et al., (1993) Intravitreal Pharmacokinetics of Liposome-encapsulated Arnikacin in a Rabbit Model. Opthamology 100: 1640-1644.

Zhang et al., (1999) A Novel Method to Prepare Liposomes Containing Arnikacin. Journal Microencapsulation 16(4): 511-516.

Beaulac et al., "Eradication of Mucoid *Pseudomonas aeruginosa* with Fluid Liposome-Encapsulated Tobramycin in an Animal Model of Chronic Pulmonary Infection," Antimicrobial Agents and Chemotherapy, 40(3):665-669 (1996).

Beaulac et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).

Deol et al., "Lung specific stealth liposomes: stability, biodistribution and toxicity of liposomal antitubular drugs in mice," Biochemica et Biophysica Acta, 1334:161-172 1997).

Xiu et al., "Drug Resistant Analysis of *Pseudomonas aeruginosa* in Patients with Mechanical Ventilation," Med. J. Chin. PLA, 27(6):544-545 (2002).

Schreier, et al.; "Pulmonary delivery of liposomes," Journal of Controlled Release, 24: 209-223 (1993).

* cited by examiner

US 7,879,351 B2

HIGH DELIVERY RATES FOR LIPID BASED DRUG FORMULATIONS, AND METHODS OF TREATMENT THEREOF

RELATED APPLICATIONS

This application is a continuation-in-part of U.S. patent application Ser. No. 11/185,448, filed Jul. 19, 2005, which is a continuation-in-part of U.S. patent application Ser. No. 11/023,971, filed Dec. 28, 2004, which is a continuation-in-part of U.S. patent application Ser. No. 10/696,389, filed Oct. 29, 2003, which claims the benefit of U.S. Provisional Patent Application Ser. No. 60/421,923, filed Oct. 29, 2002.

BACKGROUND OF THE INVENTION

Certain sustained release technology suitable for administration by inhalation employs lipid based formulations such as liposomes to provide prolonged therapeutic effect of drug in the lung and systemically by sustained release and the ability to target and enhance the uptake of drug into sites of disease.

For a lipid based drug delivery system, it is often desirable to lower the lipid-to-drug (L/D) ratio as much as possible to minimize the lipid load to avoid saturation effects in the body. For lung delivery by inhalation, this may be particularly true because for chronic use, dosing of lipid could outpace clearance thus limiting the administration and thus effectiveness of the drug product. A lower L/D ratio would allow more drug to be given before the dosing/clearance threshold is met.

SUMMARY OF INVENTION

It is an object of the present invention to provide lipid based drug formulations with low lipid to drug ratios.

It is also an object of the present invention to provide a method of preparing lipid based drug formulations with low lipid to drug ratios.

It is also an object of the present invention to provide a method of delivering lipid based drug formulations at high delivery rates as measured by mg/min of the drug.

It is also an object of the present invention to provide a method of treating a patient for a pulmonary infection comprising administering to the patient in need thereof a therapeutically effective amount of a lipid based drug formulation comprising a low L/D ratio wherein the drug is an antiinfective.

The subject invention results from the realization that lipid based drug formulations with low L/D ratios are achieved by preparing them using coacervation techniques.

Via methods disclosed herein, liposomes of modest size (<1 μm) comprising entrapped drug at L/D weight ratios of typically about 0.40-0.49:1 are created. The captured volumes of liposomes have been measured, and from these numbers one is able to calculate what the theoretical entrapment should be if the drug behaved as an ideal solute (i.e., does not interact with the liposome membrane but entraps ideally along with water). From this comparison, entrapment numbers that are 3-5× higher than expected are observed, indicating that a special interaction is occurring that allows greater than expected entrapment, and lower than expected L/D ratios. The solutions in which the liposomes form have a given drug concentration. The concentration of drug inside the liposomes should be about the same concentration as in the solution. However, internal drug concentrations are calculated at least about 3× greater. It has now been discovered that this phenomenon can be explained by the formation of a drug coacervate which initiates lipid bilayer formation around the drug coacervate.

In part the present invention relates to a method of preparing a lipid based active agent formulation comprising mixing a lipid and an active agent with a coacervate. In a further embodiment, the coacervate is formed prior to mixing with the lipid. In a further embodiment, the coacervate is formed during mixing with a lipid. In a further embodiment, the coacervate is formed after mixing with a lipid. In a further embodiment, the coacervate is a coacervate of the active agent. In a further embodiment, the coacervate is a coacervate of a third component other that the lipid and active agent. In a further embodiment, the third component comprises a counter ion capable of exchanging with the active agent.

In a further embodiment, the third component is a charged polymer. In a further embodiment, the charged polymer is an acrylate and the counter ion is an ammonium counter ion. In a further embodiment, the active agent is added after mixing the lipid with the coacervate and the active agent exchanges with the counter ion.

In a further embodiment, the third component is an ion capable of complexing with the active agent. In a further embodiment, the ion is a metal ion. In a further embodiment, the metal ion is $Mg^{2+}$. In a further embodiment, the active agent is added after mixing the lipid with the coacervate and the active agent coordinates to the ion.

In a further embodiment, the lipid is added as a solution with an organic solvent. In a further embodiment, the lipid is added as an aqueous micellar suspension with a surfactant. In a further embodiment, the lipid is induced to precipitate by diluting the micellar suspension with an aqueous solution to below the critical micellar concentration (CMC) of the surfactant.

In a further embodiment, the lipid is induced to precipitate by changing the pH.

In part the present invention relates to a method of preparing a lipid based drug formulation comprising mixing a lipid with a drug coacervate. In a further embodiment the lipid is dissolved in an organic solvent forming a lipid solution, and the drug coacervate forms from mixing an aqueous solution of the drug with the lipid solution. In a further embodiment the lipid solution and aqueous drug solution are mixed from two separate streams in an inline fashion. In a further embodiment the two streams enter a Y or T-connector prior to mixing in line. In a further embodiment a third stream of water or salt water is added to dilute the resulting lipid and drug mixture. In a further embodiment the organic solvent is ethanol.

In a further embodiment, the present invention relates to the aforementioned method wherein the lipid solution is added at a rate of 1 L/min and the aqueous drug solution is added at a rate of 1.5 L/min. In a further embodiment the lipid solution is added at a rate of 1 L/min, the aqueous drug solution is added at a rate of 1.5 L/min, and the water or salt water is added at a rate of 1 L/min.

In a further embodiment, the present invention relates to the aforementioned method wherein the lipid is a mixture of a phospholipid and a sterol. In a further embodiment the phospholipid is dipalmitoylphosphatidylcholine (DPPC) and the sterol is cholesterol. In a further embodiment the DPPC: cholesterol ratio is 2:1 by weight. In a further embodiment the lipid solution is at 20 mg/ml and the aqueous drug solution is at 75 mg/ml.

In a further embodiment, the present invention relates to the aforementioned method wherein the drug is an antiinfective. In a further embodiment the antiinfective is selected from the following: an aminoglycoside, a tetracycline, a sulfonamide, p-aminobenzoic acid, a diaminopyrimidine, a quinolone, a β-lactam, a β-lactam and a β-lactamase inhibitor, chloraphenicol, a macrolide, penicillins, cephalosporins, corticosteroid, prostaglandin, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or combination thereof. In a further embodiment the antiinfective is an aminoglycoside. In a further embodiment the aminoglycoside is amikacin. In a further embodiment the aminoglycoside is tobramicin. In a further embodiment the aminoglycoside is gentamicin.

In another embodiment the present invention relates to a lipid based drug formulation wherein the lipid to drug ratio is 0.40-0.49:1 by weight. In a further embodiment the lipid based formulation is a liposome. In a further embodiment, the drug is an antiinfective. In a further embodiment the antiinfective is selected from the following: an aminoglycoside, a tetracycline, a sulfonamide, p-aminobenzoic acid, a diaminopyrimidine, a quinolone, a β-lactam, a β-lactam and a β-lactamase inhibitor, chloraphenicol, a macrolide, penicillins, cephalosporins, corticosteroid, prostaglandin, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or combination thereof. In a further embodiment the antiinfective is an aminoglycoside. In a further embodiment the aminoglycoside is amikacin. In a further embodiment the aminoglycoside is tobramicin. In a further embodiment the aminoglycoside is gentamicin.

In a further embodiment the lipid comprises a mixture of a phospholipid and a sterol. In a further embodiment the phospholipid is DPPC and the sterol is cholesterol. In a further embodiment the DPPC and the cholesterol is in a 2:1 ratio by weight.

In another embodiment, the present invention relates to a method of delivering a lipid based drug formulation at a rate of 10 to 25 mg/min of drug comprising nebulizing the aforementioned lipid based drug formulations of the present invention using a compressor pressure of 20 to 40 psi. In a further embodiment, the entrapped drug retention of greater than 45%. In a further embodiment the lipid based drug formulation has an L/D ratio of less than 0.49.

In another embodiment, the present invention relates to a method of treating a patient for a pulmonary infection comprising administering to the patient a therapeutically effective amount of the aforementioned lipid based drug formulations. In a further embodiment the lipid based drug formulation has an L/D ratio of less than 0.49. In a further embodiment the pulmonary infection is a pseudomonas, *P. aeruginosa, P. paucimobilis, P. putida, P. fluorescens*, and *P. acidovorans*, staphylococcal, Methicillinresistant *Staphylococcus aureus* (MRSA), streptococcal, *Streptococcus pneumoniae, Escherichia coli, Klebsiella, Enterobacter, Serratia, Haemophilus, Yersinia pesos, Burkholderia pseudomallei, B. cepacia, B. gladioli, B. multivorans, B. vietnamiensis, Mycobacterium tuberculosis, M. avium complex* (MAC), *M. avium, M. intracellulare, M. kansasii, M. xenopi, M. marinum, M. ulcerans, M. fortuitum* complex, *M. fortuitum*, or *M. chelonei* infection.

In another embodiment, the present invention relates to a method of treating a patient for a pulmonary infection caused by cystic fibrosis (CF) comprising administering to the patient a therapeutically effective amount of the aforementioned lipid based drug formulations.

These embodiments of the present invention, other embodiments, and their features and characteristics, will be apparent from the description, drawings and claims that follow.

DETAILED DESCRIPTION

Figure 1:
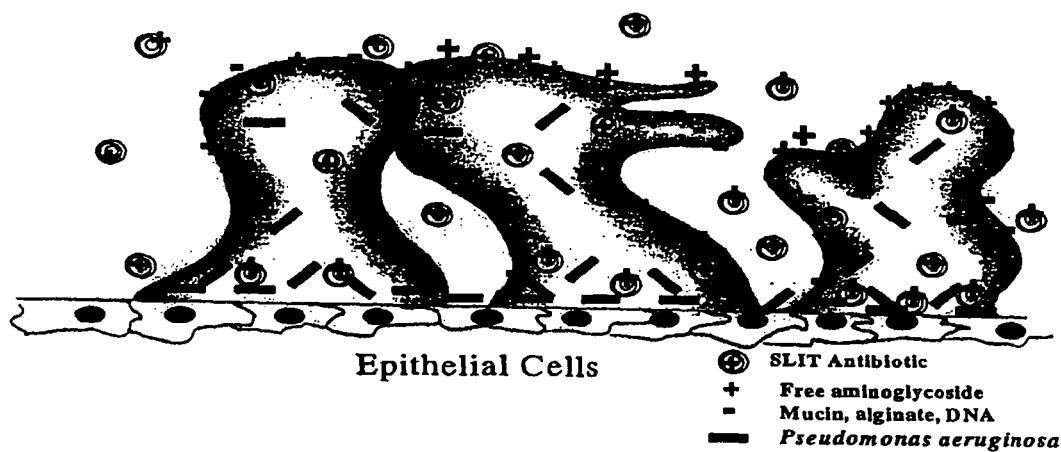
FIG. 1 depicts the cross sectional diagram of the sputum/biofilm seen in patients with cystic fibrosis.

The present invention discloses a lipid drug formulation prepared by forming a drug coacervate which induces lipid bilayer formation around the drug. The method results in low lipid to drug ratios for the resulting lipid drug formulation and inner drug concentrations that are 3 to 5× higher than the external drug concentration used. The present invention also discloses a method of preparing these lipid formulations using coacervation techniques, high delivery rates for administering these lipid drug formulations via nebulization, and methods of treating pulmonary infections comprising administering these lipid drug formulations to a patient in need thereof.

1. Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e. to at least one) of the grammatical object of the article. By way of example, "an element" means one element or more than one element.

The term "bioavailable" is art-recognized and refers to a form of the subject invention that allows for it, or a portion of the amount administered, to be absorbed by, incorporated to, or otherwise physiologically available to a subject or patient to whom it is administered.

The terms "comprise" and "comprising" are used in the inclusive, open sense, meaning that additional elements may be included.

The term "drug" is art-recognized and refers to any chemical moiety that is a biologically, physiologically, or pharmacologically active substance that acts locally or systemically in a subject. Examples of drugs, also referred to as "therapeutic agents", are described in well-known literature references such as the Merck Index, the Physicians Desk Reference, and The Pharmacological Basis of Therapeutics, and they include, without limitation, antiinfectives, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The terms "encapsulated" and "encapsulating" are refers to adsorption of drugs on the surface of lipid based formulation, association of drugs in the interstitial region of bilayers or between two monolayers, capture of drugs in the space between two bilayers, or capture of drugs in the space surrounded by the inner most bilayer or monolayer.

The term "including" is used herein to mean "including but not limited to". "Including" and "including but not limited to" are used interchangeably.

The term "lipid antiinfective formulation," or "Lip-antiinfective," or "Lip-An" discussed herein is any form of antiinfective composition where at least about 1% by weight of the antiinfective is associated with the lipid either as part of a complex with the lipid, or as a liposome where the antibiotic may be in the aqueous phase or the hydrophobic bilayer phase or at the interfacial headgroup region of the liposomal bilayer. Preferably, at least about 5%, or at least about 10%, or at least about 20%, or at least about 25%, can be so associated. Association can be measured by separation through a filter where lipid and lipid-associated antiinfective is retained and free antiinfective is in the filtrate. A "liposomal antiinfective formulation" is a lipid antiinfective formulation wherein the lipid formulation is the form of a liposome.

The term "mammal" is known in the art, and exemplary mammals include humans, primates, bovines, porcines, canines, felines, and rodents (e.g., mice and rats).

A "patient," "subject" or "host" to be treated by the subject method may mean either a human or non-human animal.

The term "pharmaceutically-acceptable salts" is art-recognized and refers to the relatively non-toxic, inorganic and organic acid addition salts of compounds, including, for example, those contained in compositions of the present invention.

The term "solvent infusion" is a process that includes dissolving one or more lipids in a small, preferably minimal, amount of a process compatible solvent to form a lipid suspension or solution (preferably a solution) and then adding the solution to an aqueous medium containing bioactive agents. Typically a process compatible solvent is one that can be washed away in a aqueous process such as dialysis. The composition that is cool/warm cycled is preferably formed by solvent infusion, with ethanol infusion being preferred. Alcohols are preferred as solvents. "Ethanol infusion," a type of solvent infusion, is a process that includes dissolving one or more lipids in a small, preferably minimal, amount of ethanol to form a lipid solution and then adding the solution to an aqueous medium containing bioactive agents. A "small" amount of solvent is an amount compatible with forming liposomes or lipid complexes in the infusion process. The term "solvent infusion" may also include an in-line infusion process where two streams of formulation components are mixed in-line.

The term "substantially free" is art recognized and refers to a trivial amount or less.

The term "surfactant" as used herein refers to a compound which lowers the surface tension of water by adsorbing at the air-water interface. Many surfactants can assemble in the bulk solution into aggregates that are known as micelles. The concentration at which surfactants begin to form micelles is known as the "critical micelle concentration" or CMC. Lipids useful for the current application may also be surfactants with extremely low CMC. Micelle-forming surfactants useful for the current application should have a CMC higher than the CMC of the lipid. At concentrations above CMC the micelle-forming surfactants can form mixed micelles composed of surfactants and lipid molecules. Upon dilution below CMC, micelle-forming surfactants will dissociate into a true solution thus leaving lipid molecules exposed to the aqueous medium. This leads to spontaneous precipitation of lipids, preferably in a form of bilayers.

The phrase "therapeutically effective amount" as used herein means that amount of a compound, material, or composition comprising a lipid drug formulation according to the present invention which is effective for producing some desired therapeutic effect by inhibiting pulmonary infections.

The term "treating" is art-recognized and refers to curing as well as ameliorating at least one symptom of any condition or disease. The term "treating" also refers to prophylactic treating which acts to defend against or prevent a condition or disease.

2. Coacervation

Coacervation in its simplest form can be thought of as a heaping together. In more technical terms, coacervation is the separation into two liquid phases in colloidal systems. The phase more concentrated in the colloid component (drug) is called the coacervate, and the other phase is the equilibrium solution.

The term colloidal refers to a state of subdivision, implying that the molecules or polymolecular particles dispersed in a medium have at least in one direction a dimension roughly between 1 nm and 1 µm, or that in a system discontinuities are found at distances of that order. IUPAC Compendium of Chemical Terminology 1972, 31, 605.

A solution of macromolecules is a simple and the most common Colloid system. Small molecules also can form association colloids as reversible aggregates. An association colloid is a reversible chemical combination due to weak chemical bonding forces wherein up to hundreds of molecules or ions aggregate to form colloidal structures with sizes of from about 1 to about 2000 nanometers or larger.

Current classification of coacervation phenomenon is based on the mechanism driving the separation of two phases. Gander B, Blanco-Prieto M. J., Thomasin C, Wandrey Ch. and Hunkeler D., Coacervation/Phase Separation, In: Encyclopedia of Pharmaceutical Technology, Vol. 1, Swarbrick J, Boylan J. C., Eds., Marcel Dekker, 2002, p. 481-497). They include:

1. Coacervation induced by partial desolvation. This in turn can involve a binary system of a solvent and a polymer, where coacervation inducing factors are temperature or pH. Or it can be a ternary system including a solvent, a polymer, and a coacervating agent (nonsolvent for the polymer or electrolyte (salt)). This type of Coacervation is often called Simple Coacervation. Classical example of Simple Coacervation is coacervation of gelatin solution by adding alcohol (nonsolvent for gelatin). Other nonsolvents useful to induce coacervation in aqueous systems may include propanol, isopropanol, ecetone, dioxane. When electrolytes are used for polymer desolvation, the phenomenon is called salting-out. In aqueous systems the ability of ions to cause dehydration follows the Hofmeister or lyotropic series $NH4^+<K^+<Na^+<Ca^{2+}<Mg^{2+}<Al^{3+}$ for cations, and $Cl^-<SO4^{2-}<tartrate^{2-}$, $phosphate^{2-}<citrate^{3-}$, in order of increasing salting-out capacity.
2. Coacervation induced by Polymer-Polymer repulsion. In this type, the second polymer added to the solution of the first polymer induces phase separation with the $1^{st}$ polymer being in the coacervate phase suspended in a phase of the $2^{nd}$ polymer. An example of Polymer-Polymer repulsion is PLA coacervation in dichloromethane solvent induced by silicone oil.
3. Coacervation induced by non-covalent polymer cross-linking ("Complex Coacervation"). The cross-linking agent can be a polymer of opposite charge to the coacervating polymer, or di- or trivalent counter-ion to the polymer, such as $Ca^{2+}$, $Mg^{2+}$, $Al^{3+}$, $Zn^{2+}$, $Tartrate^{2-}$ and others. Typical polymers used in complex coacervation include: polyanions Alginate, Carrageenan, Carboxymethylcellulose, Chondroitin sulfate, Cellulose sulfate, Gellan, Hyaluronic acid, Poly(acrylic acid), Xanthan; polycations Chitosan, Poly(diallyldimethylammonium chloride), Poly(L-lysine), Poly(vinylamine). In general, polyanion-polycation ineraction is controlled by a number of parameters, such as charge density, type of ionic group, chain architecture. In addition, pH, ionic strength, concentrations, temperature influence the complex formation.

Obviously, a combination of the listed above types can be used to control coacervation. Particularly, nonsolvent addition in combination with cross-linking agents, or nonsolvent and desalting agents.

Figure 10:
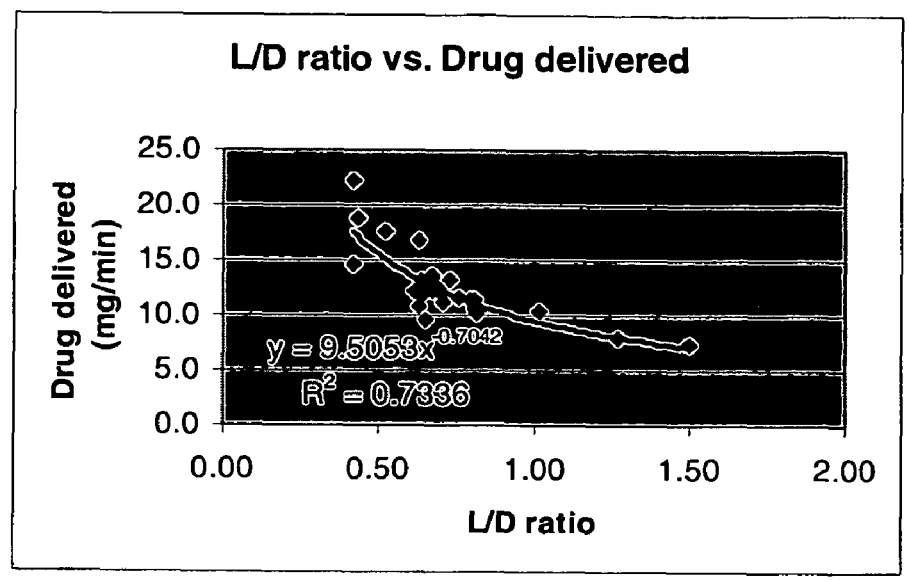
FIG. 10 depicts a graph of drug delivery rate v. L/D ratio showing that the lower the L/D ratio, the higher the drug delivery rate that can be achieved.
Figure 11:
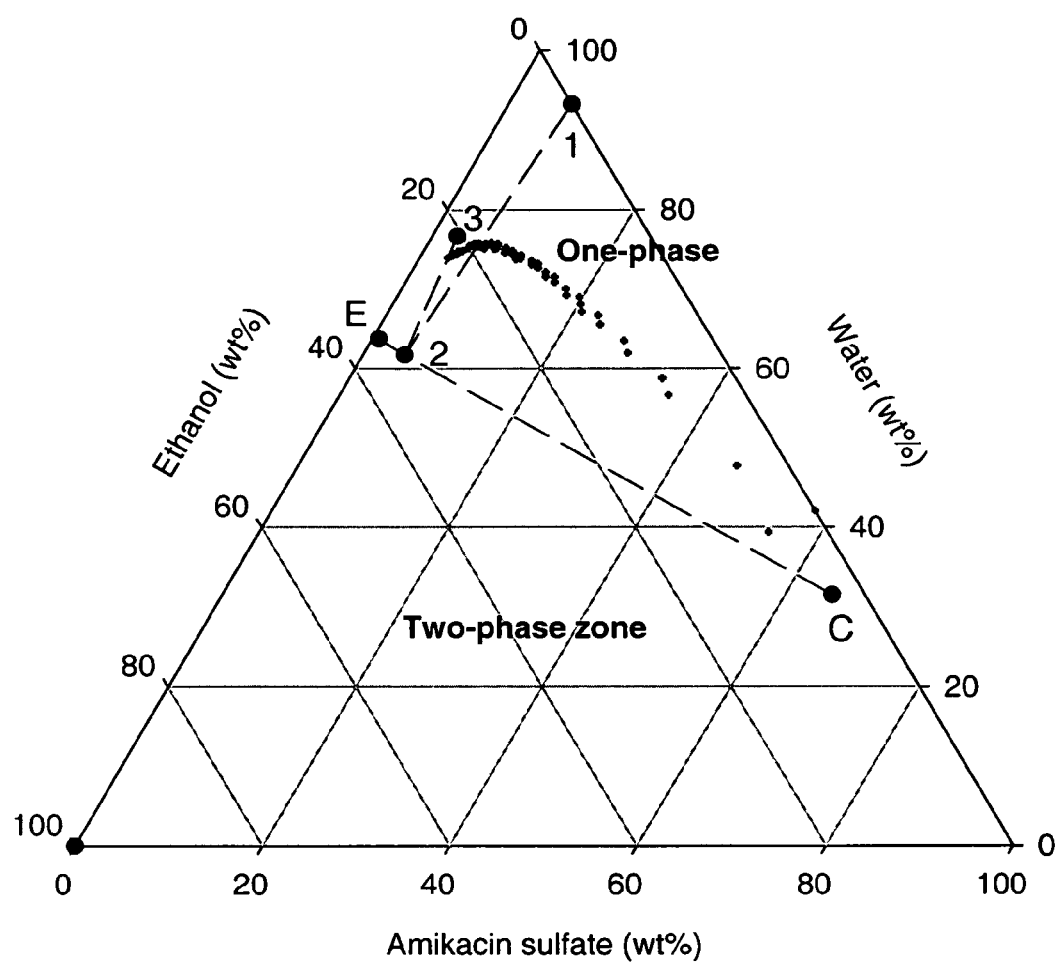
FIG. 11 depicts a ternary phase diagram of amikacin sulfate-water-ethanol system.

FIG. 10 depicts a ternary phase diagram for an amikacin sulfate-water-ethanol system. The two-phase area under the binodial curve is a zone where the system separates into two phases, a coacervate phase and an equilibrium phase. The area above the binodial curve is a zone where single liquid phase system of amikacin sulfate dissolved in water-ethanol mixture exists. When 3 parts of amikacin sulfate solution in water at 70 mg/mL (point 1) is mixed with 2 parts of ethanol, the resulting mixture has composition (point 2), which spontaneously separates into two phases: coacervate phase rich in amikacin (point C) and equilibrium phase pour in amikacin (point E). Coacervate phase comprises only about 4.5% of total volume and originally forms as small droplets suspended in equilibrium phase. If lipids are present in surrounding solution when coacervates are just formed, they can spontaneously form bilayers around those droplets. During manufacturing it is often desired to limit exposure of the product to high ethanol concentration. For examples, another 3 parts of saline or buffer can be added consequently to the mixture, which shifts composition to the single-phase zone (point 3). Since at that point liposomes are already formed encapsulating majority of coacervate phase material, amikacin will stay encapsulated inside the liposomes.

It is key that the methods and lipid formulations of the present invention are not prepared passively, i.e encapsulation is not carried out by equilibrium alone. Coacervate formation leads to higher internal drug concentrations relative to external drug concentrations and lower L/A ratios.

3. Drug

The drug coacervate can conceivably occur with any type of drug. Preferably, the drug is a water soluble antiinfective. Antiinfectives are agents that act against infections, such as bacterial, mycobacterial, fungal, viral or protozoal infections. Antiinfectives covered by the invention include but are not limited to aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), sulfonamides (e.g., sulfanilamide, sulfadiazine, sulfamethoxazole, sulfisoxazole, sulfacetamide, and the like), paraaminobenzoic acid, diaminopyrimidines (such as trimethoprim, often used in conjunction with sulfamethoxazole, pyrazinamide, and the like), quinolones (such as nalidixic acid, cinoxacin, ciprofloxacin and norfloxacin and the like), penicillins (such as penicillin G, penicillin V, ampicillin, amoxicillin, bacampicillin, carbenicillin, carbenicillin indanyl, ticarcillin, aziocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil; cefmetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chlorampherii-col, macrolides (such as erythromycin, azithromycin, clarithromycin, and the like), lincomycin, clindamycin, spectinomycin, polymyxin B, polymixins (such as polymyxin A, B, C, D, E1 (colistin A), or E2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Antiinfectives can include antifungal agents, including polyene antifungals (such as amphotericin B, nystatin, natamycin, and the like), flucytosine, imidazoles (such as n-ticonazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed. Discussion and the examples are directed primarily toward amikacin but the scope of the application is not intended to be limited to this antiinfective. Combinations of drugs can be used.

Particularly preferred antiinfectives include the aminoglycosides, the quinolones, the polyene antifungals and the polymyxins. Particularly preferred aminoglycosides include amikacin, gentamicin, and tobramycin.

Also included as suitable antiinfectives used in the lipid drug formulations of the present invention are pharmaceutically acceptable addition salts and complexes of drugs. In cases wherein the compounds may have one or more chiral centers, unless specified, the present invention comprises each unique racemic compound, as well as each unique nonracemic compound.

In cases in which the drugs have unsaturated carbon-carbon double bonds, both the cis (Z) and trans (E) isomers are within the scope of this invention. In cases wherein the drugs may exist in tautomeric forms, such as keto-enol tautomers, such as

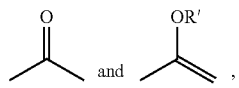

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included as suitable drugs used in the lipid antiinfective formulations of the present invention are prodrugs of the drug compounds. Prodrugs are considered to be any covalently bonded carriers which release the active parent compound in vivo.

4. Pulmonary Infections

The lipid drug formulations of the present invention with their low L/D ratios are particularly useful for treating pulmonary infections when the drug is an antiinfective. Among the pulmonary infections (such as in cystic fibrosis patients) that can be treated with the methods of the invention are *Pseudomonas* (e.g., *P. aeruginosa, P. paucimobilis, P. putida, P. fluorescens*, and *P. acidovorans*), staphylococcal, Methicillinresistant *Staphylococcus aureus* (MRSA), streptococcal (including by *Streptococcus pneumoniae*), *Escherichia coli, Klebsiella, Enterobacter, Serratia, Haemophilus, Yersinia pesos, Burkholderia pseudomallei, B. cepacia, B. gladioli, B. multivorans, B. vietnamiensis, Mycobacterium tuberculosis, M. avium* complex (MAC)(*M. avium* and *M. intracellulare*), *M. kansasii, M. xenopi, M. marinum, M. ulcerans,* or *M. fortuitum* complex (*M. fortuitum* and *M. chelonei*) infections.

5. Methods of Treatment

In one embodiment the present invention comprises a method of treating a patient for a pulmonary infection comprising administering to the patient in need thereof a therapeutically effective amount of a lipid drug formulation with a low L/D ratio wherein the drug is an antiinfective.

Where no specific dosage is provided below, the preferred dosage of the invention is 50% or less, 35% or less, 20% or less, or 10% or less, of the minimum free drug (which of course can be a salt) amount that is effective, if delivered to the lungs via a nebulizer, to reduce the CFU count in the lungs by one order of magnitude over the course of a 14-day treatment. The comparative free drug amount is the cumulative amount that would be used in the dosing period applied with the drug administration of the invention. The comparative minimum free drug defined in this paragraph is a "comparative free drug amount."

The non-CF treating embodiments of the invention can be used with any animal, though preferably with humans. Relative amounts in a given animal are measured with respect to such animal.

The dosing schedule is preferably once a day or less. In preferred embodiments, the dosing schedule is once every other day, every third day, every week, or less. For example, the dosing schedule can be every other day or less, using 50% or less of the comparative free drug amount. Or, for example, the dosing can be daily using 35% or less of the comparative free drug amount. See FIGS. 3 and 4 for animal data showing that lipid antiinfective formulations are more efficacious than the free drug.

To treat infections, the effective amount of the antiinfective will be recognized by clinicians but includes an amount effective to treat, reduce, ameliorate, eliminate or prevent one or more symptoms of the disease sought to be treated or the condition sought to be avoided or treated, or to otherwise produce a clinically recognizable change in the pathology of the disease or condition. Amelioration includes reducing the incidence or severity of infections in animals treated prophylactically. In certain embodiments, the effective amount is one effective to treat or ameliorate after symptoms of lung infection have arisen. In certain other embodiments, the effective amount is one effective to treat or ameliorate the average incidence or severity of infections in animals treated prophylactically (as measured by statistical studies).

Liposome or other lipid delivery systems can be administered for inhalation either as a nebulized spray, powder, or aerosol, or by intrathecal administration. Inhalation administrations are preferred. The overall result is a less frequent administration and an enhanced therapeutic index compared to free drug or parenteral form of the drug. Liposomes or other lipid formulations are particularly advantageous due to their ability to protect the drug while being compatible with the lung lining or lung surfactant.

The present invention includes methods for treatment of pulmonary gram-negative infections. One usefully treated infection is chronic pseudomonal infection in CF patients. Known treatments of lung infections (such as in CF patients) with aminoglycoside generally comprise administering approximately 200-600 mg of amikacin or tobramycin per day via inhalation. The present invention allows for treatment by administering, in one preferred embodiment, 100 mg or less of amikacin per day (or normalized to 100 mg per day or less if dosing less frequent). In yet another embodiment, administration of 60 mg or less of amikacin every day is performed. And in still another embodiment administration of approximately 30 to 50 mg not more than once every 2 days is performed. The most preferred embodiment comprises administration of approximately 30 to 50 mg every other day or every third day.

6. Lipids and Liposomes

The lipids used in the compositions of the present invention can be synthetic, semi-synthetic or naturally-occurring lipids, including phospholipids, tocopherols, steroids, fatty acids, glycoproteins such as albumin, anionic lipids and cationic lipids. The lipids may be anionic, cationic, or neutral. In one embodiment, the lipid formulation is substantially free of anionic lipids. In one embodiment, the lipid formulation comprises only neutral lipids. In another embodiment, the lipid formulation is free of anionic lipids. In another embodiment, the lipid is a phospholipid. Phosholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC). Other examples include dimyristoylphosphatidylcholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoyl-stearoylphosphatidylcholine (PSPC) and palmitoyl-stearoylphosphatidylglycerol (PSPG), driacylglycerol, diacylglycerol, seranide, sphingosine, sphingomyelin and single acylated phospholipids like mono-oleoyl-phosphatidylethanol amine (MOPE).

The lipids used can include ammonium salts of fatty acids, phospholipids and glycerides, steroids, phosphatidylglycerols (PGs), phosphatidic acids (PAs), phosphotidylcholines (PCs), phosphatidylinositols (PIs) and the phosphatidylserines (PSs). The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9(Z)-octadecenyloxy)-prop-1-yl-N,N,N-trimethylammonium chloride (DOTMA) and 1,2-bis(oleoyloxy)-3-(trimethylammonio)propane (DOTAP). Examples of steroids include cholesterol and ergosterol. Examples of PGs, PAs, PIs, PCs and PSs include DMPG, DPPG, DSPG, DMPA, DPPA, DSPA, DMPI, DPPI, DSPI, DMPS, DPPS and DSPS, DSPC, DPPG, DMPC, DOPC, egg PC.

Liposomal antiinfective formulations composed of phosphatidylcholines, such as DPPC, aid in the uptake by the cells in the lung such as the alveolar macrophages and helps to sustain release of the antiinfective agent in the lung (Gonzales-Rothi et al. (1991)). The negatively charged lipids such as the PGs, PAs, PSs and PIs, in addition to reducing particle aggregation, can play a role in the sustained release characteristics of the inhalation formulation as well as in the transport of the formulation across the lung (transcytosis) for systemic uptake. The sterol compounds are believed to affect the release and leakage characteristics of the formulation.

Liposomes are completely closed lipid bilayer membranes containing an entrapped aqueous volume. Liposomes can be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase. Lipid antiinfective formulations are associations lipid and the antiinfective agent. This association can be covalent, ionic, electrostatic, noncovalent, or steric. These complexes are non-liposomal and are incapable of entrapping additional water soluble solutes. Examples of such complexes include lipid complexes of amphotencin B (Janoff et al., Proc. Nat Acad. Sci., 85:6122 6126, 1988) and cardiolipin complexed with doxorubicin.

A lipid clathrate is a three-dimensional, cage-like structure employing one or more lipids wherein the structure entraps a bioactive agent. Such clathrates are included in the scope of the present invention.

Proliposomes are formulations that can become liposomes or lipid complexes upon coming in contact with an aqueous liquid. Agitation or other mixing can be necessary. Such proliposomes are included in the scope of the present invention.

7. Methods of Preparation

The process for forming lipid drug formulations involves a "solvent infusion" process. This is a process that includes dissolving one or more lipids in a small, preferably minimal, amount of a process compatible solvent to form a lipid suspension or solution (preferably a solution) and then infusing the solution with an aqueous medium containing the drug. Typically a process compatible solvent is one that can be washed away in a aqueous process such as dialysis or diafiltration. "Ethanol infusion," a type of solvent infusion, is a process that includes dissolving one or more lipids in a small, preferably minimal, amount of ethanol to form a lipid solution and then infusing the solution with an aqueous medium containing the drug. A "small" amount of solvent is an amount compatible with forming liposomes or lipid complexes in the infusion process. It is key that the conditions for the infusion process have to lead to coacervate formation. Ultimate conditions for infusing a given lipid solution with a given aqueous solution of the active agent have to be determined based on the Examples presented herein and the effect of various parameters taught below. Also useful to someone of ordinary skill in the art, are the techniques for forming coacervates as described in such references as Bunderberg de Jong, H. G., Kruyt, H. R. Koazevation (Entmischung in Kolloidalen Systemen), Koll. Zeitsch. 1930, 50(10), 39-48; Gander B, Blanco-Prieto M. J., Thomasin C, Wandrey Ch. and Hunkeler D., Coacervation/Phase Separation. In: Encyclopedia of Pharmaceutical Technology, Vol. 1, Swarbrick J, Boylan J. C., Eds., Marcel Dekker, 2002, p. 481-497; Newton D. W. Coacervation: Principles and Applications. In: Polymers for Controlled drug delivery. Tarcha P. J., Ed., CRC Press, Boca Raton, 1991, 67-81; Scott P. W., Williams A. C., Barry B. W., Characterization of complex coacervates of Some Tricyclic Antidepressants and evaluation of their potential for Enhancing Transdermal Flux. J. Controlled Release 1996, 41 (3), 215-227; Thomasin C., Merkle H. P., Gander B. Drug microencapsulation by PLA/PLGA Coacervation in the Light of Thermodynamics. 2. Parameters determining Microsphere Formation. J. Pharm Sci. 1998, 87 (30), 269-275; Ball V., Winterhalter M., Schwinte P., Lavalle Ph., Voegel J.-C., Schaal P. Complexation mechanism of Bovine Serum Albumin and Poly(allylamine hydrochloride). J. Phys. Chem. B. 2002, 106, 2357-2364; Mohanty B., Bohidar H. B. Systematic of Alcohol-Induced Simple Coacervation in Aqueous Gelatin Solutions. Biomacromolecules 2003, 4, 1080-1086, all of which are incorporated herein by reference in their entirety. Preferably, the step is performed by an in-line infusion process.

Liposome or lipid formulation sizing can be accomplished by a number of methods, such as extrusion, sonication and homogenization techniques which are well known, and readily practiced, by ordinarily skilled artisans. Extrusion involves passing liposomes, under pressure, one or more times through filters having defined pore sizes. The filters are generally made of polycarbonate, but the filters may be made of any durable material which does not interact with the liposomes and which is sufficiently strong to allow extrusion under sufficient pressure. Preferred filters include "straight through" filters because they generally can withstand the higher pressure of the preferred extrusion processes of the present invention. "Tortuous path" filters may also be used. Extrusion can also use asymmetric filters, such as Anopore™ filters, which involves extruding liposomes through a branched-pore type aluminum oxide porous filter.

Liposomes or lipid formulations can also be size reduced by sonication, which employs sonic energy to disrupt or shear liposomes, which will spontaneously reform into smaller liposomes. Sonication is conducted by immersing a glass tube containing the liposome suspension into the sonic epicenter produced in a bath-type sonicator. Alternatively, a probe type sonicator may be used in which the sonic energy is generated by vibration of a titanium probe in direct contact with the liposome suspension. Homogenization and milling apparatii, such as the Gifford Wood homogenizer, Polytron™ or Microfluidizer, can also be used to break down larger liposomes or lipid formulations into smaller liposomes or lipid formulations.

The resulting liposomal formulations can be separated into homogeneous populations using methods well known in the art; such as tangential flow filtration. In this procedure, a heterogeneously sized population of liposomes or lipid formulations is passed through tangential flow filters, thereby resulting in a liposome population with an upper and/or lower size limit. When two filters of differing sizes, that is, having different pore diameters, are employed, liposomes smaller than the first pore diameter pass through the filter. This filtrate can the be subject to tangential flow filtration through a second filter, having a smaller pore size than the first filter. The retentate of this filter is a liposomal/complexed population having upper and lower size limits defined by the pore sizes of the first and second filters, respectively.

Mayer et al. found that the problems associated with efficient entrapment of lipophilic ionizable bioactive agents such as antineoplastic agents, for example, anthracyclines or vinca alkaloids, can be alleviated by employing transmembrane ion gradients. Aside from inducing greater uptake, such transmembrane gradients can also act to increase drug retention in the liposomal formulation.

Lipid drug formulations have a sustained effect and lower toxicity allowing less frequent administration and an enhanced therapeutic index. In preclinical animal studies and in comparison to inhaled tobramycin (not-liposomal or lipid-based) at the equivalent dose level, liposomal amikacin was shown to have, during the time period shortly after administration to over 24 hours later, drug levels in the lung that ranged from two to several hundred times that of tobramycin. Additionally, liposomal amikacin maintained these levels for well over 24 hours. In an animal model designed to mimic the pseudomonas infection seen in CF patients, liposomal amikacin was shown to significantly eliminate the infection in the animals' lungs when compared to free aminoglycosides.

Lung surfactant allows for the expansion and compression of the lungs during breathing. This is accomplished by coating the lung with a combination of lipid and protein. The lipid is presented as a monolayer with the hydrophobic chains directed outward. The lipid represents 80% of the lung surfactant, the majority of the lipid being phosphatidylcholine, 50% of which is dipalmitoyl phosphatidylcholine (DPPC) (Veldhuizen et al, 1998). The surfactant proteins (SP) that are present function to maintain structure and facilitate both expansion and compression of the lung surfactant as occurs during breathing. Of these, SP-B and SP-C specifically have lytic behavior and can lyse liposomes (Hagwood et al., 1998; Johansson, 1998). This lytic behavior could facilitate the gradual break-up of liposomes. Liposomes can also be directly ingested by macrophages through phagocytosis (Couveur et al., 1991; Gonzales-Roth et al., 1991; Swenson et al, 1991). Uptake of liposomes by alveolar macrophages is another means by which drugs can be delivered to the diseased site.

The lipids preferably used to form either liposomal or lipid formulations for inhalation are common to the endogenous lipids found in the lung surfactant. Liposomes are composed of bilayers that entrap the desired drug. These can be configured as multilamellar vesicles of concentric bilayers with the drug trapped within either the lipid of the different layers or the aqueous space between the layers. The present invention utilizes unique processes to create unique liposomal or lipid drug formulations. Both the processes and the product of these processes are part of the present invention.

In one particularly preferred embodiment, the lipid drug formulations of the present invention are prepared by an in-line infusion method where a stream of lipid solution is mixed with a stream of drug solution in-line. For example, the two solutions may be mixed in-line inside a mixing tube preceded by a Y or T-connector. In this way, the in-line infusion method creates the best conditions for forming a drug coacervate. This infusion method results in lower lipid to drug ratios and higher encapsulation efficiencies.

In another particularly preferred embodiment, the lipid drug formulations of the present invention are prepared by vortexing a lipid-organic solvent solution with an aqueous drug solution at a suitable vortexing level.

Another novel method of preparing the lipid drug formulations of the present invention involves initially encapsulating a charged polymer by way of forming a coacervate with the charged polymer in the presence of a lipid. It is believed that this technique will lead to low lipid to charged polymer ratios in the same way that low lipid to drug ratios are obtained. Drug is introduced into the interior of the lipid formulation via ion exchange across the lipid membrane between the charged drug and counter ions of the charged polymer. This technique, not including coacervation formation, is known as "remote loading." Examples of remote loading are disclosed in U.S. Pat. Nos. 5,316,771 and 5,192,549, both of which are incorporated herein by reference in their entirety.

The processes described above may be further improved by optimizing parameters such as flow rate, temperature, activation agent concentration, and salt addition after infusion step. The following experiments do not necessarily represent the methods of the present invention as indicated by the higher lipid to drug ratios. Rather they represent a set of experiments for testing the effect of the aforementioned parameters. The multiple variables give one an idea of the novelty behind using coacervation techniques to form lipid based drug formulations with low L/D ratios.

7.1 Effect of Flow Rates

Individual flow rates were varied while keeping the total flow rate at 800 mL/min. To do so, separate pumps were used set at different pumping rates. The mixed solutions were infused for 10 s into a beaker containing NaCl solution such that the final NaCl concentration was 1.5% and the final ethanol concentration did not exceed 30%. After mixing, a 1 mL aliquot was run though a Sephadex G-75 gel filtration column to separate free amikacin from encapsulated. A 1 mL fraction with highest density (determined by visual turbidity) was collected for further analysis. The results are presented in Table 1. Increasing the lipid/amikacin flow rate ratio resulted in an almost constant L/D until 300/500 mL/min. With further increase of lipid rate, L/D started to increase and particle size also started getting larger. At the same time, higher lipid flow rates gave better amikacin recovery (encapsulation efficiency) as more lipid mass was added.

TABLE 1

Effect of flow rates on amikacin encapsulation.*

| Batch | Flow rates mL/min AMK | Flow rates mL/min Lipid | AMK total mg/mL | AMK free % | Lipid mg/mL | L/D | VOL Size | AMK Recovery % |
|---|---|---|---|---|---|---|---|---|
| 1 | 600 | 200 | 1.38 | 5.3 | 1.25 | 0.91 | 289 | 14.7 |
| 2 | 550 | 250 | 1.80 | 5.1 | 1.90 | 1.06 | 305 | 17.2 |
| 3 | 500 | 300 | 2.18 | 5.2 | 2.29 | 1.05 | 314 | 22.8 |
| 4 | 450 | 350 | 1.27 | 5.8 | 1.47 | 1.16 | 388 | 26.8 |
| 5 | 400 | 400 | 1.05 | 6.1 | 1.69 | 1.61 | 471 | 24.9 |

*Lipid and amikacin solutions were kept at 40° C. Amikacin stock solution was 50 mg/mL. NaCl 10% solution was added before infusion to obtain final 1.5%. Infusion time was set at 10 s. Mixing tube 10 cm; 6-element in-line mixer positioned at 0 cm.

Batch 3 with the lipid/amikacin flow rates of 300/500 mL/min showed the best L/D and particle, combined with reasonably high amikacin recovery. Thus it was decided to use these flow rates for all further experiments.

In order to reproduce the results at chosen conditions a fully washed batch (batch 6) using diafiltration was prepared as presented in Table 2. NaCl 10% solution was added into the beaker prior to infusion to make the final concentration 2% (as compared to 1.5% in the batches in Table 1). The resulting L/D (1.71) was not as good as in batch 3 in Table 1 and the particle size was higher. This may be due to an adverse effect of high NaCl concentration contacting liposomes in the early stages of liposome formation. Samples separated (washed) using gel-filtration columns tend to have better L/D than ones washed by diafiltration. This may have to do with the different degree of stress liposomes experience, or simply samples separated on the gel filtration column contained a fraction of liposomes with better L/D which does not represent the whole population.

TABLE 2

Summary of the fully washed batches. Process parameters varied were: temperatures, amikacin stock concentration, and other (see Table 3 below). All batches were concentrated to nearly a maximum extent, until the inlet pressure reached 10 PSI.

| Batch | Temp, C. L/AMK/W | AMK stock mg/mL | AMK total mg/mL | AMK free % | Lipid mg/mL | L/D | Size VOL nm | Size SD % |
|---|---|---|---|---|---|---|---|---|
| 6 | 40/40/30 | 50 | 36.1 | 2.7 | 61.8 | 1.71 | 392 | 43.4 |
| 8 | 50/RT/30 | 50 | 48.5 | 9.6 | 49.3 | 1.02 | 332 | 32.0 |
| 9 | 50/RT/30 | 50 | 41.6 | 5.1 | 43.2 | 1.04 | 359 | 34.4 |
| 10 | 50/RT/30 | 50 | 53.1 | 10.2 | 34.4 | 0.65 | 350 | 28.6 |
| 11 | 50/RT/30 | 40 | 20.7 | 4.8 | 46.9 | 2.27 | 407 | 35.9 |
| 12 | 50/RT/30 | 40 | 81.0 | 1.9 | 49.4 | 0.61 | 341 | 33.0 |
| 13 | 50/RT/30 | 30 | 68.6 | 1.7 | 62.5 | 0.91 | 311 | 22.4 |
| 14 | 50/RT/30 | 40 | 79.6 | 1.6 | 47.8 | 0.60 | 346 | 37.2 |
| 15 | 50/RT/30 | 40 | 71.3 | 2.0 | 42.3 | 0.59 | 353 | 33.4 |
| 16 | 30/30/30 | 40 | 61.9 | 6.1 | 51.5 | 0.83 | 369 | 28.4 |
| 17 | 30/30/30 | 40 | 73.8 | 2.4 | 57.2 | 0.77 | 362 | 32.6 |
| 18 | 30/30/30 | 40 | 74.4 | 2.3 | 54.0 | 0.73 | 549 | 61.7 |

*The 3$^{rd}$ column represents the temperatures of Lipid and Amikacin solutions just before infusion, and the temperature during washing (diafiltration). RT = room temperature. "VOL size" is the volume weighted particle size.

TABLE 3

Processing conditions for batches 1-18.*

| Batch | Mixing tube cm | Mixer position cm | NaCl added Stock % | NaCl added Volume parts | Timing to infusion | Washing conditions NaCl % | Washing conditions 1st wash |
|---|---|---|---|---|---|---|---|
| 1-5 | 10 | 0 | VAR | VAR | before | 1.5 | (Seph column) |
| 6 | 10 | 0 | 10 | 200 | before | 1.5 | diafiltration |
| 7 | 10 | 5 | 10 | 100 | before | 1.5 | (Seph column) |
| 8 | 10 | 5 | 10 | 150 | during | 1.5 | diafiltration |
| 9 | 10 | 5 | 10 | 150 | during | 1.5 | diafiltration |
| 10 | 10 | 5 | 10 | 100 | 5' after | 1.5 | 2x dilution |
| 11 | 10 | 5 | 10 | 150 | imm after | 1.5 | 2x dilution |
| 12 | 10 | 5 | H2O | 180 | 20" after | 1.5 | 2x dilution |
| 13 | 10 | 5 | H2O | 180 | 30" after | 1.5 | 2x dilution |
| 14 | 10 | 5 | H2O | 180 | 30" after | 1.5 | diafiltration |
| 15 | 10 | 5 | 1.5 | 180 | 30" after | 1.5 | diafiltration |
| 16 | 60 | NO | 0.9 | 180 | during | 0.9 | diafiltration |
| 17 | 60 | NO | 1.5 | 180 | during | 1.5 | diafiltration |
| 18 | 60 | 0 | 1.5 | 180 | during | 1.5 | diafiltration |

*Lipid and amikacin solutions were infused at rates 300/500 mL/min for 30 s (examples 6-10) or 20 s (examples 11-18). Additional aqueous solution (NaCl or water) was added (as parts relative to 500 parts amikacin volume).

7.2 Effects of Process Temperature

The settings were kept the same as in batch 3 except that the amount of NaCl solution added was less, making the final concentration 1.0%. Solution was added again before infusion was initiated because with the short infusion time it was difficult to make the addition during infusion. Also, during infusion the in-line mixer shifted to the end of the mixing tube under the pressure of the flow. The position of the mixer was 5 cm from the front end of the tube instead of 0 cm for batch 3. This may be important, as the L/D ratio obtained at the same temperature 40/40° C. condition in batch 20 was 0.55, almost half of that in batch 3. On comparing amikacin encapsulation at different infusion temperatures, one can see that, surprisingly, lower temperatures gave better L/D. Of the temperatures tested, lipid/amikacin temperatures 30/30° C. and 50/RT gave similar L/D ratios of 0.32 and 0.37. Again, as in batches 1-5, the numbers from these washed samples by gel-filtration were low, perhaps less than that if the batches had been washed by diafiltration.

TABLE 4

Effect of temperature on amikacin encapsulation.*

| Batch | Temperature, C. | | AMK total mg/mL | AMK free % | Lipid mg/mL | L/D | VOL Size nm |
|---|---|---|---|---|---|---|---|
| | Lipid | AMK | | | | | |
| 19 | 30 | 30 | 4.88 | 2.8 | 1.54 | 0.32 | 278 |
| 20 | 40 | 40 | 3.62 | 1.5 | 1.98 | 0.55 | 335 |
| 21 | 50 | 50 | 3.50 | 1.8 | 2.74 | 0.78 | 309 |
| 22 | 50 | RT | 5.27 | 2.9 | 1.93 | 0.37 | 342 |

*Lipid and amikacin solutions were infused at rates 300/500 mL/min for 10s. Amikacin stock solution was 50 mg/mL. NaCl 10% solution was added before infusion to obtain final 1.0% concentration. Mixing tube 10 cm; 6-element in-line mixer positioned at 5 cm.

In separate experiments it was found that mixing of 90% ethanol and water at either 30° C. and 30° C. or 50° C. and 22° C., respectively, resulted in a similar final temperature of nearly 36° C. This suggests that the temperature of the final mixture rather than that of the individual components is important for amikacin encapsulation. The temperatures 50° C./RT were used in examples 6-15. In examples 16-18 temperatures of 30° C. and 30° C. for the two streams were used with comparable results, although a little less amikacin encapsulation was observed.

7.3 Effect of Post-infusion Addition of Aqueous Volume

Attention was next focused on the steps of NaCl solution addition and the washing process. Process parameters were varied in various directions. Right after the infusion step at flow rates 300/500, ethanol concentration in the mixture reaches 34%. Amikacin has limited solubility at this concentration (see FIG. 9).

Figure 9:
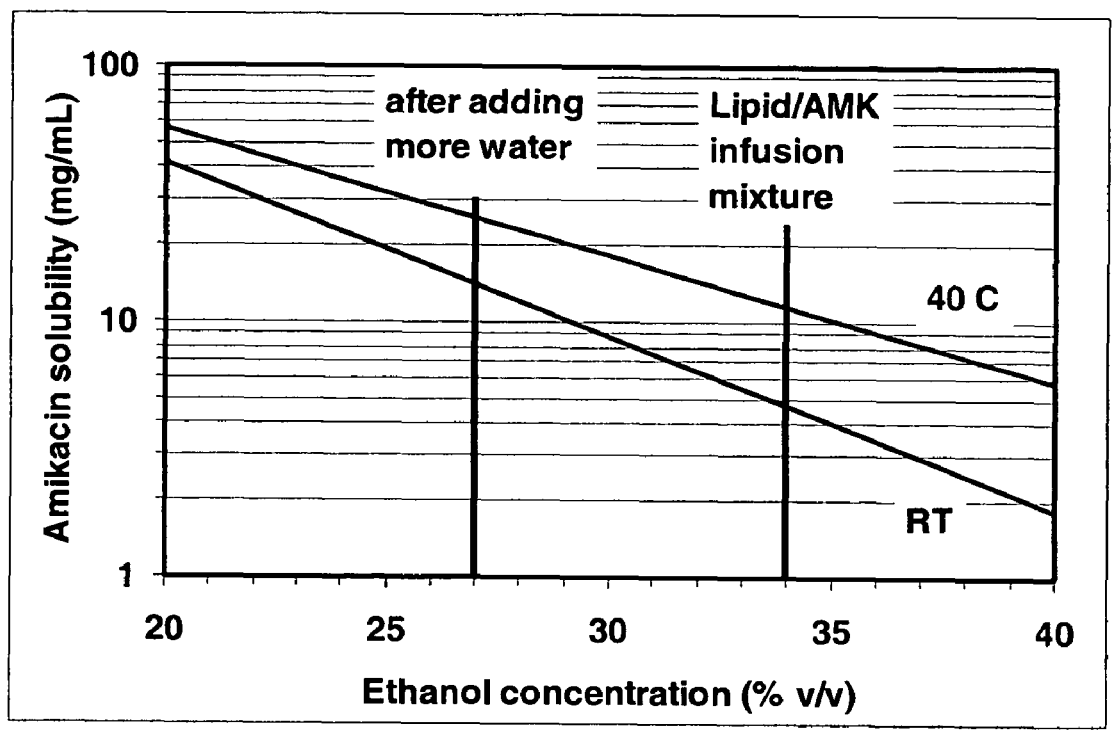
FIG. 9 depicts miscibility of amikacin sulfate with ethanol/water. Lines represent maximal amikacin concentration (base) miscible with ethanol solution at room temperature (RT) and 40° C. At higher concentrations amikacin forms a separate liquid phase (coacervates), which later precipitates as crystals. Vertical lines show ethanol concentration in the lipid/amikacin infusion mixture (300/500 parts) and after adding water 200 parts.

If one starts with 50 mg/mL amikacin stock, then after mixing with the lipid solution there will be more than 30 mg/mL total amikacin where at least half (15 mg/mL) is free amikacin, assuming 50% encapsulation efficiency. This is higher than the solubility limit at 34% ethanol. One possible solution to this problem is to add more water to the vessel with the lipid/amikacin mixture, thus reducing both ethanol and amikacin concentration. For example, adding 200 parts of water (or NaCl solution) to 800 parts of lipid/amikacin would reduce ethanol to 27% (FIG. 9). This makes amikacin soluble at 15 mg/mL or even higher depending on temperature.

In addition, adding NaCl may stabilize osmotic conditions. When liposomes are formed and amikacin is encapsulated at an internal concentration of 200-300 mg/mL, there is only ~15 mg/mL or so of amikacin not encapsulated. In the absence of saline this would create an osmotic imbalance, which in turn might lead to leakage of amikacin. Adding 150 parts of 10% NaCl to 800 parts of lipid/amikacin will result in about 1.5% NaCl final concentration (outside liposomes).

A number of batches were generated where different amounts of NaCl solution (or water in some batches) were added at different times relative to the infusion event (see Table 5, compiled from Tables 2 and 3). From the table a general trend can be seen, leading to the following conclusions:

Some time interval between infusion and addition of the aqueous volume is required to obtain lower L/D (if a short mixing tube is used). Of batches 6-15, those with an interval 20 s or longer had lower L/D. One possible explanation is that liposomes are not completely formed immediately after mixing of the streams. When a longer mixing tube is used (batches 16-18), which allows for a longer mixing time, the time interval is not required.

Adding a high concentration NaCl solution to balance osmolality does not actually help retain amikacin. In fact, adding pure water at an appropriate time interval resulted in the lowest L/D and total amikacin concentration.

Adding 100 parts NaCl 10% (batch 9) 5 min after infusion gave a competitive L/D ratio but did not give as good a total amikacin concentration. It may be that NaCl, when present at early stages with relatively high ethanol concentrations, leads to increased aggregation and viscosity.

TABLE 5

Role of aqueous volume and NaCl concentration added to the lipid/amikacin mixture to adjust ethanol concentration. Not all the variables shown; see Tables 2 and 3.

| | AMK | | NaCl added | | AMK | | Size |
|---|---|---|---|---|---|---|---|
| Batch | stock mg/mL | Stock % | Volume parts | Timing to infusion | total mg/mL | L/D | VOL nm |
| 6 | 50 | 10 | 200 | before | 36.1 | 1.71 | 392 |
| 8 | 50 | 10 | 150 | during | 48.5 | 1.02 | 332 |
| 9 | 50 | 10 | 150 | during | 41.6 | 1.04 | 359 |
| 10 | 50 | 10 | 100 | 5' after | 53.1 | 0.65 | 350 |
| 11 | 40 | 10 | 150 | imm after | 20.7 | 2.27 | 407 |
| 12 | 40 | $H_2O$ | 180 | 20" after | 81.0 | 0.61 | 341 |
| 13 | 30 | $H_2O$ | 180 | 30" after | 68.6 | 0.91 | 311 |
| 14 | 40 | $H_2O$ | 180 | 30" after | 79.6 | 0.60 | 346 |
| 15 | 40 | 1.5 | 180 | 30" after | 71.3 | 0.59 | 353 |
| 16 | 40 | 0.9 | 180 | during | 61.9 | 0.83 | 369 |
| 17 | 40 | 1.5 | 180 | during | 73.8 | 0.77 | 362 |
| 18 | 40 | 1.5 | 180 | during | 74.4 | 0.73 | 549 |

7.4 Effect of Antiinfective Stock Solution

Previously it was found that using 50 mg/mL amikacin stock solution produced the best entrapment. Reducing the amikacin stock concentration to 40 mg/mL increased L/D when used in conventional processes. With the two-stream in-line infusion process, ethanol concentration reaches higher levels, so the current 50 mg/mL amikacin may not be the optimal concentration.

Table 6 summarizes the effect of using various amikacin stock concentrations. 40 mg/mL delivered comparable or better L/D values, and even improved amikacin recovery. Using less amikacin relative to a constant amount of lipid, and providing a similar L/D, resulted in a higher percent encapsulation (batch 12). Further decrease of amikacin stock concentration to 30 mg/mL resulted in a slightly increased L/D, although recovery was still impressive (batch 13).

TABLE 6

Amikacin stock concentration can be reduced while improving efficiency. Amikacin recovery is calculated based on L/D obtained and assumed 100% lipid recovery.

| Batch | AMK stock mg/mL | AMK total mg/mL | AMK free % | Lipid mg/mL | L/D | Size VOL nm | AMK Recovery % |
|---|---|---|---|---|---|---|---|
| 10 | 50 | 53.1 | 10.2 | 34.4 | 0.65 | 350 | 37.0 |
| 12 | 40 | 81.0 | 1.9 | 49.4 | 0.61 | 341 | 51.2 |
| 13 | 30 | 68.6 | 1.7 | 62.5 | 0.91 | 311 | 45.7 |
| 14 | 40 | 79.6 | 1.6 | 47.8 | 0.60 | 346 | 52.0 |

Reducing amikacin stock concentration has another implication. It reduces the concentration of free amikacin in a post-infusion lipid/amikacin mixture, allowing it to remain soluble at higher ethanol concentration. Assuming that lipid and amikacin are mixed at 300/500 ratio, amikacin stock is 50 mg/mL, and encapsulation efficiency is 37%, then initial free amikacin would be ~20 mg/mL. Similarly, 40 mg/mL amikacin stock with 52% encapsulation would result in ~12 mg/mL free amikacin. 30 mg/mL amikacin stock with 46% encapsulation would result in ~10 mg/mL free amikacin.

8. Lipid to Drug Ratio

There are several ways to increase the entrapment of drug (e.g. aminoglycosides such as amikacin, tobramycin, gentamicin) in liposomes. One way is to make very large liposomes (>1 μm) where the entrapped volume per amount of lipid is large. This approach is not practical for inhalation (nebulization) of liposomes because 1) shear stress during nebulization tends to rupture liposomes in a size dependent manner where larger liposomes (>0.5 μm) suffer greater release and 2) the smaller droplet sizes necessary for good lung deposition are themselves less than about ~3 μm. So for inhalation, it is desirable to keep the liposome size as small as possible to avoid too much release. Currently, the mean diameter for the liposomes disclosed herein is less than about 0.4 μm (see Table 4).

Another approach to decrease L/D is to use negatively charged lipids. The aminoglycosides listed above are highly positively charged with 4 to 5 amines per compound. Usually sulfate salts of these aminoglycosides are used in therapeutic formulations. Along with the multi-cationic character comes strong binding to negatively charged liposomes. This results in greater entrapment during liposome formation. The purpose of antiinfective formulations is to provide sustained release to the lung environment. Rapid clearance of the liposomes by macrophage uptake would run counter to this. It has been well documented that negatively charged liposomes experience a much higher degree of uptake by macrophages than neutral liposomes. Therefore, it is desirable to use neutral liposomes.

One group of technologies that allow very high drug entrapment into small liposomes is based on gradient loading where a pH gradient, ammonium sulfate gradient, or Mg-sulfate gradient are used to load amine-drugs into liposomes: see U.S. Pat. Nos. 5,578,320 5,736,155 5,837,279 5,922,350 (pH gradient); U.S. Pat. Nos. 5,837,282 5,785,987 (Mg-sulfate gradient); and U.S. Pat. No. 5,316,771 (ammonium sulfate gradient). These techniques only work for membrane permeable amines (mono-amines where neutral form is permeable like doxorubicin and daunorubicin). Gradient loading will not work for the certain antiinfectives such as aminoglycosides as they are impermeable (too large and too highly charged).

All processes described herein can be easily adapted for large scale, aseptic manufacture. The final liposome size can be adjusted by modifying the lipid composition, concentration, excipients, and processing parameters.

The lipid to drug ratio obtained by the processes of the present invention is about 0.40 to 0.49:1. Further, the percentage of free drug, present after the product is dialyzed for a particular duration, is decreased. When the drug is a macromolecule such as a protein, the L/D ratio can be as high as about 1.2 which is low in comparison to the literature (for example, see U.S. Pat. No. 6,843,942, where encapsulation of recombinant human superoxide dismutase (rh-SOD) in a DPPC-cholesterol-stearylamine formulation was prepared with a L/D ratio of ~5).

9. Drug Delivery Rate

For a pharmaceutical inhalation therapy, it is essentially desirable to establish a high delivery rate to achieve a desired dose in a minimum dosing time. For a liposomal formulation, it is also desirable to maximize the retention of the entrapped drug during nebulization. Nebulization flow rate is the volume (or weight) of the aqueous solution that aerosolizes and flies out of the nebulizer in a unit of time (e.g. g/min, ml/min). Drug delivery rate is defined as the amount of drug that gets delivered by the nebulizer in a unit of time (e.g. mg/min).

Drug delivery efficacy can be increased by making improvements in two areas: 1) improvements in the drug delivery device, an 2) increasing the drug concentration in the drug formulation. When the drug delivery device is a jet nebulizer, key factors that affect the drug delivery rate include: model of nebulizer, i.e. structure of nebulizer, which determines the air flow rate exit from the device and aerosol droplet size; and air pressure used to propel the drug formulation. For drug formulations, drug concentration can be increased by decreasing the amount of water. By doing this, though, viscosity and surface tension increase, which has the effect of decreasing the nebulization rate.

In order to improve drug delivery rate for a given jet nebulizer, drug concentration should be increased while keeping viscosity and surface tension relatively constant. By doing this, the drug delivery rate increases even though the nebulization rate stays the same according to the formula drug delivery rate (mg/min)=drug concentration (mg/ml)×nebulization rate (ml/min).

The present invention, in part, is drawn to concentrated high dose lipid based drug formulations that provide maximal aerosol output with particle size ranges within the optimal range of 1-5 μm mass median aerodynamic diameter (MMAD).

Table 7 presents delivery rate and % drug retention data for several nebulization trials. Nebulization was carried out by a jet nebulizer for 20 min at 30 psi compressor pressure.

TABLE 7

Compositions and characteristics of liposomal amikacin delivery rates greater than 10 mg/min and retention of entrapped drug greater than 45%.

| Lot | DPPC/ cholesterol (mol %) | Salinity % | [Amikacin] mg/ml | [Lipid] mg/ml | Lipid/ Drug | Viscosity (cP) | Flow Rate mg/min | Delivery Rate mg/min | % Drug |
|---|---|---|---|---|---|---|---|---|---|
| A | 50/50 | 0.9 | 65.0 | 53.3 | 0.82 | 24.9 | 0.157 | 10.2 | 57.0 |
| B | 50/50 | 3.0 | 58.7 | 59.8 | 1.02 | N/D* | 0.177 | 10.4 | 71.5 |
| C | 60/40 | 1.5 | 76.8 | 48.8 | 0.64 | 38.5 | 0.153 | 11.8 | 50.6 |
| D | 50/50 | 1.5 | 81.6 | 54.6 | 0.67 | 35.4 | 0.164 | 13.4 | 52.8 |
| E | 50/50 | 1.5 | 78.2 | 55.0 | 0.70 | 24.9 | 0.173 | 13.5 | 57.5 |
| F | 60/40 | 1.5 | 75.5 | 50.7 | 0.67 | 27.5 | 0.180 | 13.6 | 47.4 |
| G | 50/50 | 1.5 | 80.3 | 47.8 | 0.60 | 14.2 | 0.170 | 13.7 | 68.0 |
| H | 50/50 | 3.0 | 108.1 | 69.0 | 0.64 | 25.5 | 0.154 | 16.6 | 85.0 |
| I | 50/50 | 3.0 | 107.0 | 44.6 | 0.42 | 22.1 | 0.180 | 19.3 | 68.1 |
| J | 50/50 | 3.0 | 117.8 | 56.4 | 0.48 | 31.1 | 0.175 | 20.6 | 65.2 |
| K | 50/50 | 3.0 | 130.3 | 54.2 | 0.42 | 34.8 | 0.170 | 22.2 | 68.1 |

One can see that as the L/D ratio decreases from lots A and B to the L/D ratios of the present invention obtained in lots I, J, and K, the concentration of drug also increases. At a nearly constant flow rate, an increase in drug concentration gives the highest drug delivery rate of ~19 to 22 mg/min. These results are graphed in FIG. 10.

10. Results 10.1. Biofilm Barriers of Pulmonary Infections

An obstacle to treating infectious diseases such as *Pseudomonas aeruginosa*, the leading cause of chronic illness in CF patients is drug penetration within the sputum/biofilm barrier on epithelial cells (FIG. 1). In FIG. 1, the donut shapes represent a liposomal antiinfective formulation, the "+" symbol represents free antiinfective, the "–" symbol mucin, alginate and DNA, and the solid bar symbol represents *Pseudomonas aeruginosa*. This barrier is composed of both colonized and planktonic *P. aeruginosa* embedded in alginate or exopolysaccharides from bacteria, as well as DNA from damaged leukocytes, and mucin from lung epithelial cells, all possessing a net negative charge (Costerton, et al., 1999). This negative charge binds up and prevents penetration of positively charged drugs such as aminoglycosides, rendering them biologically ineffective (Mendelman et al., 1985). Entrapment of antiinfectives within liposomal or lipid formulations could shield or partially shield the antiinfectives from non-specific binding to the sputum/biofilm, allowing for liposomal or lipid formulations (with entrapped aminoglycoside) to penetrate (FIG. 1).

Amikacin has been shown to have a high degree of resistance to bacterial enzymes, thus providing a greater percent of susceptible clinical isolates than found for other aminoglycosides including tobramycin and gentamicin (Price et al., 1976). In particular, *P. aeruginosa* isolates are far more sensitive to amikacin than other aminoglycosides while exhibiting no cross-resistance (Damaso et al., 1976).

Figure 2:
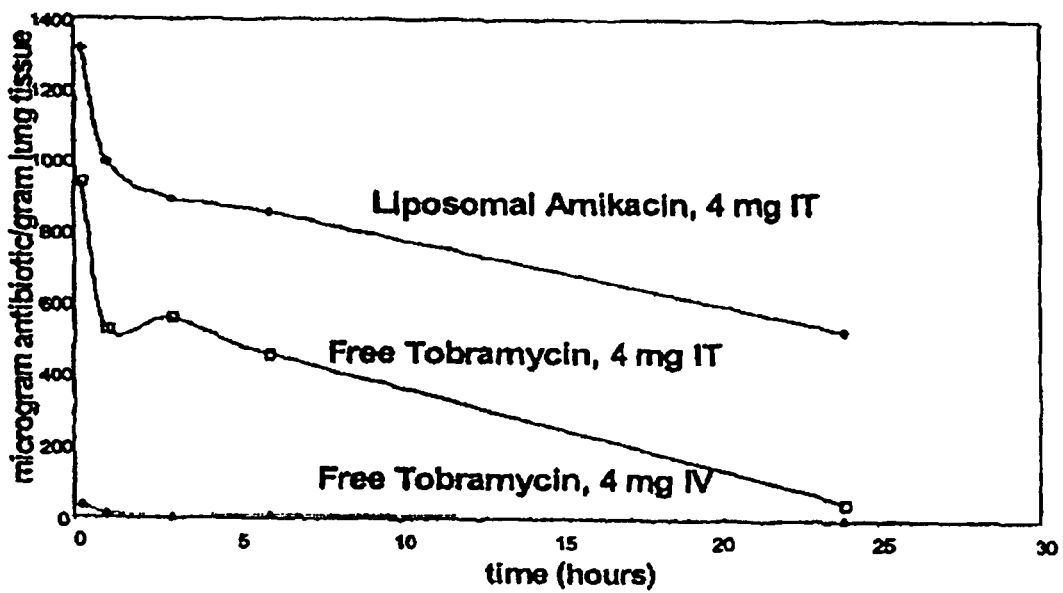
FIG. 2 depicts the graphical representation of the targeting and depot effect of the drug of the present invention.

The sustained release and depot effect of liposomal formulations of amikacin is clearly seen in FIG. 2. In this study rats were given tobramycin via intratracheal and intravenous administration. The rats were also given liposomal formulations of amikacin intratracheally at the same dose (4 mg/rat). The data show that it is only with the liposomal formulation of amikacin that a sustained release and depot effect is achieved. In fact, 24 hours after dosing, only liposomal formulations of amikacin show significant levels of the drug in the animal's lungs, while both tobramycin formulations revealed negligible levels, primarily due, it is believed to rapid systemic absorption. This greater than a hundred-fold increase of aminoglycoside in the lung for liposomal antiinfective formulations supports the idea of a sustained release liposomal formulation antiinfective that can be taken significantly less often than the currently approved TOBI® formulation (a tobramycin inhalation solution made by the Chiron Corporation, Ameryville, Calif.).

Moreover, the presence of a sputum/biofilm prevents the penetration of the free aminoglycosides due to binding of the antiinfectives to its surface (FIG. 1). Therefore, doses in excess of 1,000 gm of tobramycin/gram of lung tissue are needed to show a therapeutic effect in CF patients. This is overcome with liposomal formulations of amikacin. Thus, the therapeutic level of drug is maintained for a longer period of time in the liposomal formulations of amikacin compared to free tobramycin. This facilitation of binding and penetration could also be a means by which liposomal formulations of amikacin could significantly reduce bacterial resistance commonly seen to develop when antibacterials are present in vivo at levels below the minimum inhibitory concentration.

10.2. Pharmacokinetics

The pharmacokinetics of amikacin was determined in rats following intratracheal (IT) administration of either free tobramycin or liposomal formulations of amikacin. These data were compared to the distribution obtained in the lungs following a tail vein injection of free tobramycin. In all cases a dose of 4 mg/rat was administered. As can be seen in FIG. 2, a much larger deposition of aminoglycoside can be delivered by IT compared to injection. The depot effect of liposomal antiinfective technology is also demonstrated in that in comparison to tobramycin given either IT or IV, a greater than a hundred-fold increase in drug for liposomal formulations of amikacin still remains in the lungs twenty-four hours following administration. Thus, the therapeutic level of drug is maintained for a longer period of time in the liposomal formulations of amikacin compared to free tobramycin.

The binding of aminoglycosides to sputum of CF patients is a concern, particularly if this binding reduces the bioactivity of the antiinfective (Hunt et al., 1995). To determine whether liposomal formulations of amikacin can retain biological activity over a prolonged period of time, normal rats were administered liposomal formulations of amikacin by intratracheal instillation. This was followed by its removal at 2 or 24 hours via a bronchial alveolar lavage (BAL) to determine biological activity. Samples were concentrated by ultrafiltration followed by filtration (0.2 micron) to remove contaminating lung microbes. Amikacin concentration was determined employing a TDX instrument and biological activity determined using a Mueller Hinton broth dilution assay (*Pseudomonas aeruginosa*). The results are shown in Table 7.

TABLE 7

Results showing that liposomal formulations of amikacin retain biological activity over a prolonged period of time.

| time (hours) | amikacin in BAL (μg/mL) | amikacin in filtrate (μg/mL) | MIC (μg/mL) |
|---|---|---|---|
| 2 | 160 | 119 | 1.9 |
| 24 | 73 | 32 | 4.0 |

As shown by the above table, the recovered filtered liposomal formulation of amikacin was capable of killing *P. aeruginosa* in a Mueller Hinton broth assay even after 24 hours with an MIC of 4. At 2 hours an MIC of 2 was obtained, which is similar to that obtained for the filtered liposomal/complexed amikacin stock. Thus, the liposomal formulation of amikacin was still active following 24 hours in the lung. At 24 hours free tobramycin at the same dose was undetectable in a BAL. This indicates that not only is the liposomal antiinfective formulation retained in the lung, but it is also freely available to penetrate a sputum/biofilm over time. These data combined with the facts as evident in FIG. 2 and Table 9 (below), that liposomal formulations of amikacin release the free antiinfective over time while maintaining high levels of the antiinfective in the lungs, supports the rationale that this system may yield a sustained antiinfective effect over time. This effect should prove significant in reducing both the bioburden of the *Pseudomonas* and the development of resistance due to trough levels of antiinfective.

As an in vitro demonstration of slow release of liposomal formulation of amikacin and its sustained antiinfective effect, the formulation was incubated in sputum from patients with Chronic Obstructive Pulmonary Disease (COPD) containing PAOI mucoid *Pseudomonas*. The liposomal formulation of amikacin was also incubated in alginate containing PAO1 mucoid *Pseudomonas*. In both cases sustained and enhanced killing of the *Pseudomonas* over time was observed, as shown in Table 8.

TABLE 8

In vitro killing of *Pseudomonas* over time.

In vitro Sputum/Alginate Assay
(% survival of PA01 Mucoid *Pseudomonas*)

|  |  | Incubation time at 37° C. | | | | Amikacin conc. |
|---|---|---|---|---|---|---|
|  |  | 1 h | 3 h | 6 h | 24 | (μg/mL) |
| Lip-An-15 | Sputum | 81 | 15 | 22 | <1 | 8 |
| Lip-An-15 | Alginate | 100 | 59 | 1 | <1 | 10 |

Classical kill curves are not applicable for liposomal antiinfective formulation technology because the liposomal formulations exhibit a slow release of antiinfective with an enhanced antiinfective effect. The liposomal formulation protects the amikacin from the sputum and/or alginate until its release. In time, complete killing is observed, consistent with slow release sustained antiinfective effect model with no interference or inactivation of antiinfective.

The efficacy of liposomal amikacin formulations was studied using a model for chronic pulmonary infection (Cash et al., 1979) where *P. aeruginosa*, embedded in an agarose bead matrix, was instilled in the trachea of rats. This mucoid *Pseudomonas* animal model was developed to resemble the *Pseudomonas* infections seen in CF patients. Some of the clinical correlates to CF include: a similar lung pathology; the development of immune complex disorders; and a conversion to the mucoid phenotype by *P. aeruginosa* strains (Cantin and Woods, 1999). Rat lungs were infected with over $10^7$ CFUs of a mucoid *Pseudomonas* (strain PAO1) taken from a CF patient isolate, and subsequently treated with (a) free aminoglycoside, (b) the lipid vehicle alone as non-drug control, and (c) liposomal amikacin formulation. In addition, formulations were first screened on the ability to kill in vitro *P. aeruginosa* on modified Kirby-Bauer plates.

Figure 3:
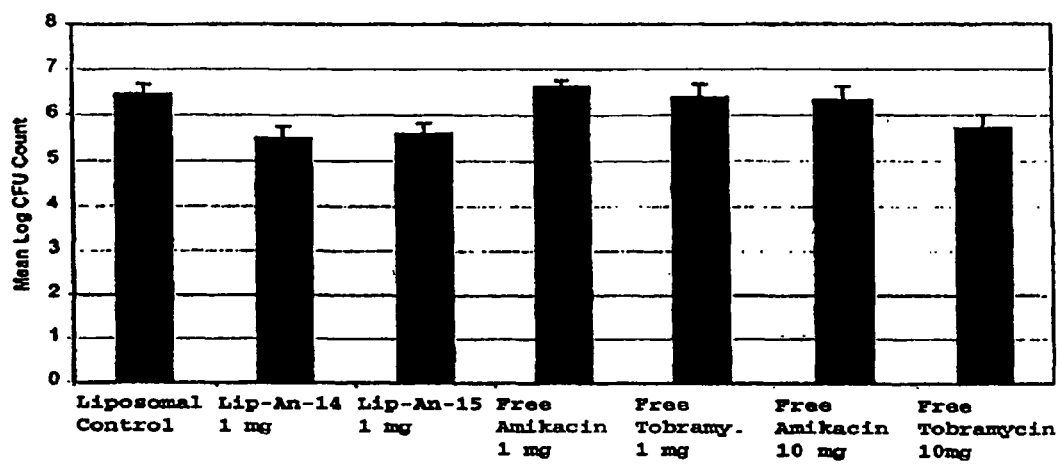
FIGS. 3 and 4 depict graphical representations of bacteriology of amikacin in various forms.
Figure 4:
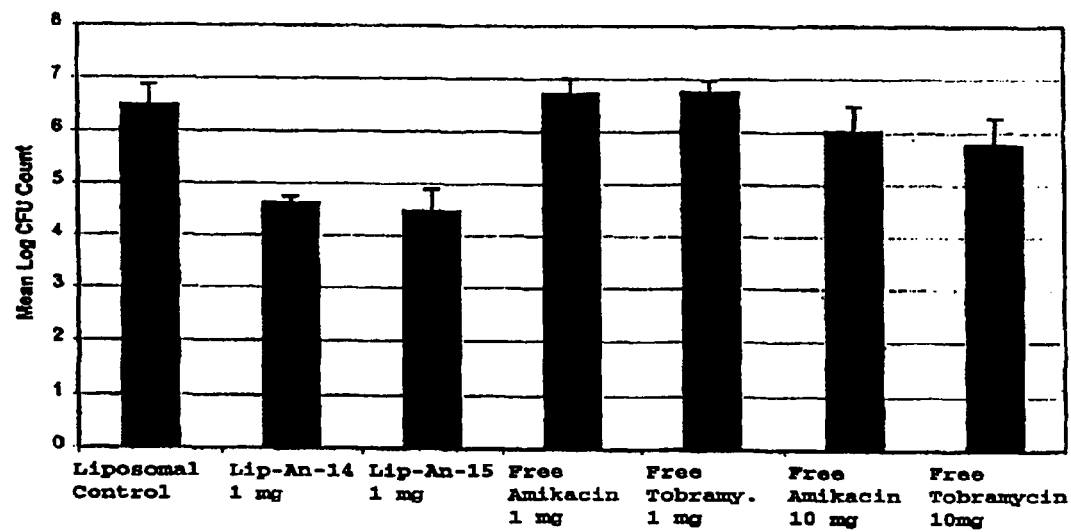

Various liposomal amikacin formulations were tested based on either different lipid compositions or manufacturing parameters resulting in different killing zones in in vitro experiments. This experiment was designed to determine the increase in efficacy obtained with liposomal aminoglycoside formulations over free aminoglycoside. Blank control lipid compositions, two different liposomal amikacin formulations and free amikacin and free Tobramycin at the same aminoglycoside concentrations as the liposomal antiinfective formulations were compared. In addition, a 10 fold higher dose of free amikacin and a 10 fold higher dose of free tobramycin were also given. Dosing was IT daily over seven days. Results (FIG. 3) indicate that liposomal amikacin in the two formulations (differing in lipid composition) revealed a significant reduction in CFU levels and were better at reducing CFUs than free amikacin or free tobramycin at 10-fold higher-dosages. In FIG. 3, Lip-An-14 is DPPC/Chol/DOPC/DOPG (42:45:4:9) and 10 mg/mL amikacin, Lip-An-15 is DDPC/Chol (1:1) also at 10 mg/mL. All lipid-lipid and lipid-drug ratios herein are weight to weight.

The next experiment (FIG. 4) was designed to demonstrate the slow release and sustained antiinfective capabilities of liposomal amikacin formulations. The dosing was every other day for 14 days, as opposed to every day for seven days as in the previous experiments. Results indicate that liposomal amikacin in the two formulations (differing in lipid composition) had a 10 to 100 times more potent (greater ability to reduce CFU levels) than free amikacin or free tobramycin. A daily human dose of 600 mg TOBI® (a tobramycin inhalation solution made by the Chiron Corporation, Ameryville, Calif.), or about 375 mg/m$^2$, corresponds to a daily rat dose of 9.4 mg. Thus the data can be directly correlated to a 10 to 100 fold improvement in human efficacy. It should be noted that a two-log reduction is the best that can be observed in this model. A 100-fold reduction in *P. aeruginosa* in sputum assays has been correlated with improved pulmonary function (Ramsey et al., 1993). The sustained release of the liposomal amikacin formulations indicate that a lower dose and/or less frequent dosing can be employed to obtain a greater reduction in bacterial growth than can be obtained with free aminoglycoside.

The efficacy of liposomal amikacin formulation was studied in a model for chronic pulmonary infection where *P. aeruginosa* was embedded in an agarose bead matrix that was instilled via the trachea of Sprague/Dawley rats. Three days later free amikacin or liposomal amikacin was dosed every day (FIG. 3) or every other day (FIG. 4) at 1 mg/rat or 10 mg/rat of the given aminoglycoside or 1 mg/rat liposomal amikacin, as well as with blank liposomes (lipid vehicle) as the control, with five rats per group.

The homogenized rat lungs (frozen) following the 14 day experiment were analyzed for aminoglycoside content and activity. The clinical chemical assay was performed using a TDX instrument while the bioassay was performed by measuring inhibition zones on agar plates embedded with *Bacillus subtilis*. The results are shown in Table 9:

TABLE 9

Results from liposomal amikacin formulation treated rat lungs infected with *P. aeruginosa*.

| Formulation | Bioassay (microgram/mL) | Clinical Assay (microgram/mL) |
|---|---|---|
| Lip-An-14 (1 mg/rat) | 9.5 | 9.1 |
| Lip-An-15 (1 mg/rat) | 21.5 | 18.4 |
| Free amikacin (10 mg/rat) | nd | 2.0 |
| Free tobramycin (10 mg/rat) | nd | 1.4 |

Drug weights are for the drug normalized to the absence of any salt form.

The Table 10 results indicate that aminoglycoside is present and active for both liposomal antiinfective formulations, while little can be detected for the free aminoglycoside even at the 10-fold higher dose. These further results establish the sustained release characteristics of liposomal antiinfective formulations, and also confirm that that antiinfective which remains is still active. Of the above formulations only the free tobramycin (0.1 microgram/mL) exhibited any detectable levels of aminoglycoside in the kidneys.

Figure 5:
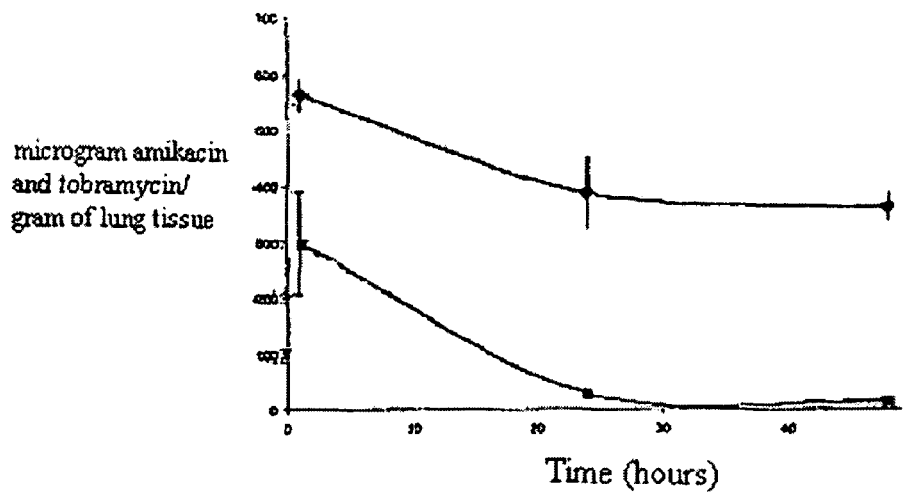
FIG. 5 depicts a graphical representation of sustained release for liposomal/complexed amikacin and tobramycin.

The sustained release and depot effect of liposomal amikacin formulation is further demonstrated in FIG. 5. Rats were given a chronic pulmonary infection where *P. aeruginosa* was embedded in an agarose bead matrix that was instilled via the trachea, using the same beads employed in the efficacy studies. The rats were then given free tobramycin or liposomal amikacin (formulation Lip-An-14) via intratracheal administration at the same dose (2 mg/rat). The data, measured in microgram antiinfective per gram lung tissue over time, show that liposomal antiinfective exhibits a sustained release and depot effect while free tobramycin revealed negligible levels in the lungs by 24 hours, primarily due it is believed to rapid systemic absorption. This greater than a hundred-fold increase of antiinfective in the lung for liposomal amikacin formulations in an infected rat supports the idea of a sustained release liposomal antiinfective that can be taken significantly less often than the currently approved TOBI® formulation (a tobramycin inhalation solution made by the Chiron Corporation, Ameryville, Calif.).

The pharmacokinetics of amikacin was determined in rats following intratracheal (IT) administration of either free tobramycin or liposomal amikacin. A dose of 2 mg/rat was administered. The depot effect of liposomal antiinfective technology is demonstrated in that in comparison to free tobramycin given IT, a greater than a hundred-fold increase in drug for liposomal amikacin still remains in the infected lungs twenty-four hours following administration. Thus, the therapeutic level of drug is maintained for a longer period of time in the liposomal formulations compared to free tobramycin.

Figure 7:
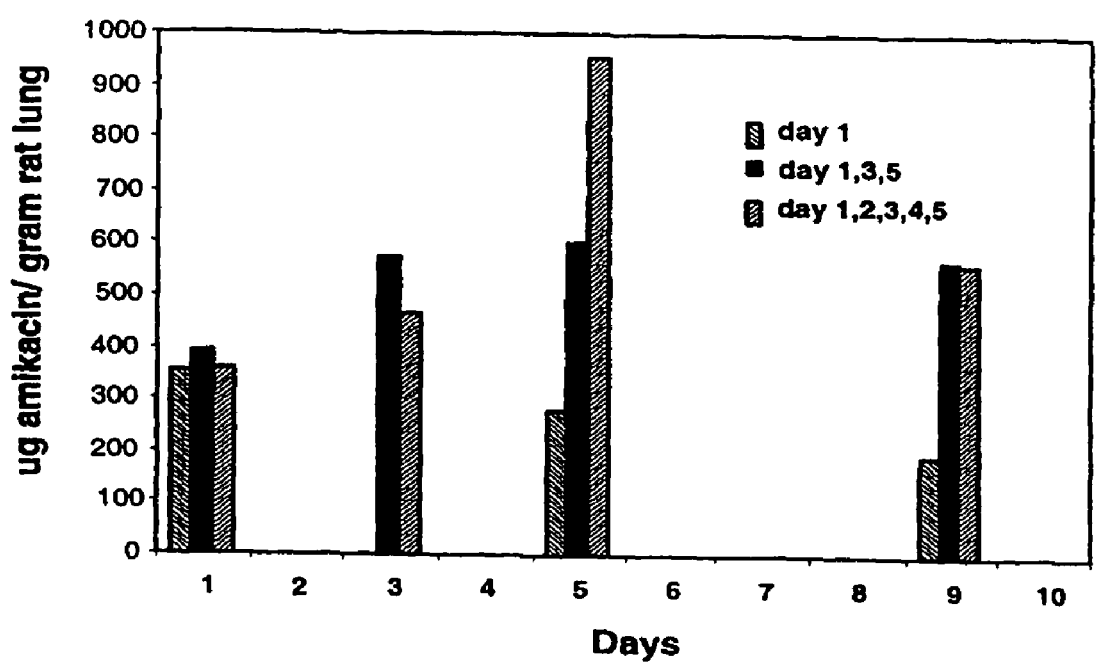
FIG. 7 depicts a graphical representation of drug residence in the lung given various dosing schedules.
Figure 8:
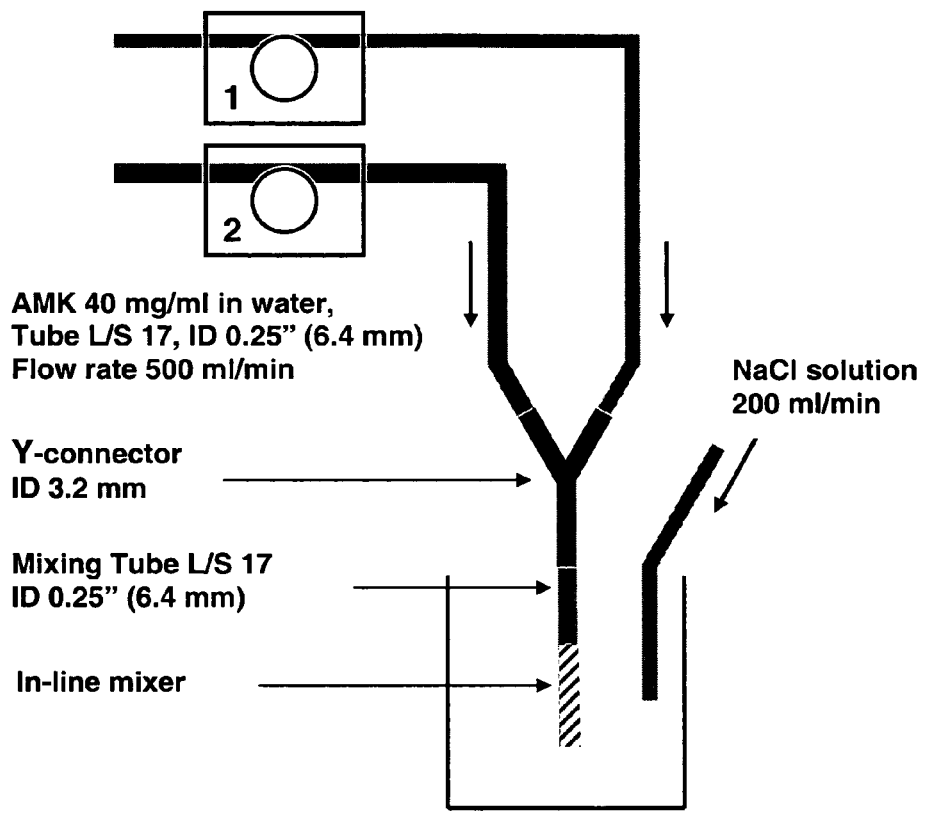
FIG. 8 depicts graphically the two-stream in-line infusion process of preparing liposomal antiinfective formulations. The flow rates depicted are non-limiting examples of flow rates subject to change as the need requires. Also, a third NaCl solution line is depicted but this may be absent or deliver just water.

FIG. 7 shows remarkable residence time and accumulation of effective amounts of antiinfective in the lungs, a result that establishes that relatively infrequent dosings can be used. Each dose is 4 hr. by inhalation (in rat, 3 rats per group, as above) of nebulized liposomal amikacin formulations (DPPC/Chol., 1:1) at 15 mg/mL amikacin. Dosing was at either day one; day one, three and five; or day one, two, three, four and five. Rats providing a given data bar were sacrificed after the respective dosing of the data bar.

Similar anti-infectives can be utilized for the treatment of intracellular infections like pulmonary anthrax and tularemia. In pulmonary anthrax the anthrax spores reach the alveoli in an aerosol. The inhaled spores are ingested by pulmonary macrophages in the alveoli and carried to the regional tracheobronchial lymph nodes or mediastinal lymph nodes via the lymphatics (Pile et al., 1998; Gleiser et al., 1968). The macrophage is central in the both the infective pathway and is the major contributor of host self-destruction in systemic (inhalation) anthrax. In addition to its attributes of sustained release and targeting, liposomal antiinfective formulation technology can enhance cellular uptake and can use alveolar macrophages and lung epithelial cells in drug targeting and delivery. The possession of these characteristics is believed to facilitate the treatment of these intracellular infections, which infections occur in the lungs and are transported by macrophages. More importantly, these characteristics should make the antiinfective more effective in that the liposomal antiinfective should be phagocytized by the very cells containing the disease. The antiinfective would be released intracellularly in a targeted manner, thereby attacking the infection before it is disseminated. The encapsulated drug can be an already approved pharmaceutical like ciprofloxacin, tetracycline, erthyromycin or amikacin. Liposomal ciprofloxacin formulations have been developed.

Figure 6:
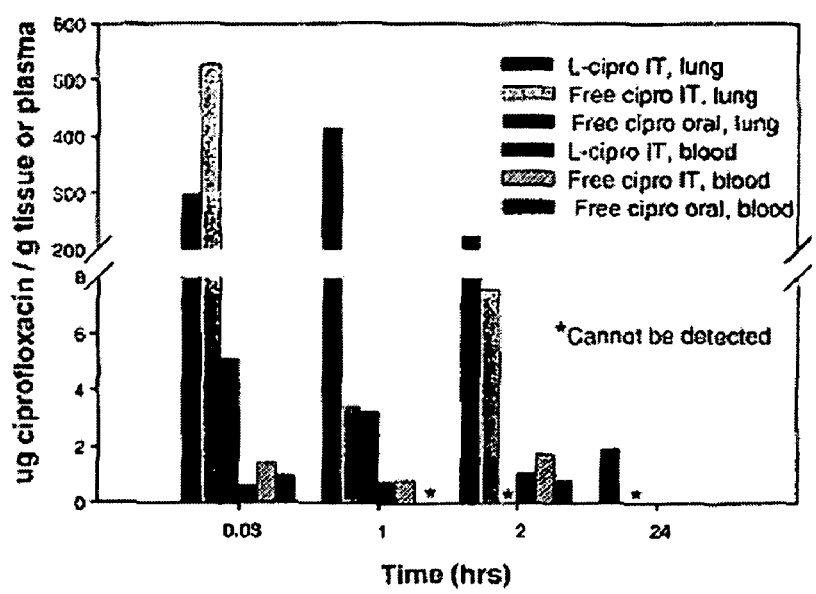
FIG. 6 depicts data on free or complexed ciprofloxacin.

In a study, this compound was administered to mice and compared to both free ciprofloxacin administered intratracheally and free ciprofloxacin administered orally, with all three compounds given at the same dose (FIG. 6). The dose for each mouse was 15 mg/kg, with three mice per group. Liposomal ciprofloxacin was in DPPC/Cholesterol (9:1), at 3 mg/mL ciprofloxacin. The lipid to drug ratio was 12.5:1 by weight. In comparison to orally administered ciprofloxacin, liposomal ciprofloxacin was present in the mice lungs at amounts over two orders of magnitude higher than free ciprofloxacin. Moreover, only liposomal ciprofloxacin showed levels of drug in the lung after 24 hours, while the orally administered drug was undetectable in less than two hours. This data supports the use of liposomal ciprofloxacin formulations and other antiinfectives like aminoglycosides, tetracyclines and macrolides for the treatment and for the prophylactic prevention of intracellular diseases used by bioterrorists.

10.4. Drug Release Mediated by *P. Aeruginosa* Infection

Release of drug in an active form in the vicinity of the infections is an important aspect of the action of liposomal drug formulation of the present invention. The potential for such targeted release was tested by monitoring the release of drug upon incubation with sputum from a CF patient, release in the lungs of rats pre-inoculated with *P. aeruginosa*, as well as the activity of against cultures of *P. aeruginosa*.

The release of amikacin by direct incubation of a culture of *P. aeruginosa* with a liposomal amikacin formulation of the present invention was previously discussed. To further investigate this phenomenon, a liposomal amikacin formulation was incubated with a preparation of sputum from a cystic fibrosis patient with *P. aeruginosa* infection. Expectorated sputum was liquefied with bovine DNase I and alginate lyase for 2 hr. at 37° C. A liposomal amikacin formulation or soluble amikacin (1 mg/mL amikacin) was mixed 1:1: with liquefied sputum or control and incubated at 37° C. with gentle shaking. Aliquots were analyzed for amikacin concentration by Abbott TDx Analyzer. Intact liposomes were lysed in a separate aliquot of each sample using a detergent, 1% Triton X-100. Supernatants from each sample were used for analysis. Over the period of 48 hours, (80-90%) of the amikacin was released in a time-dependent manner from the lipid composition under these conditions, indicating that drug release may occur at the sites of infection in the CF lung.

Release of free drug from liposomes in vivo was compared for rats that had been instilled with agar beads containing $P.$ $aeruginosa$ ($3.5 \times 10^4$ CFU/rat) versus those that had not. Three days after bead instillation, rats were allowed to inhale liposomal amikacin formulations of the present invention (approx. 6 mg/kg daily dose) every day (no bacteria group) or every other day for 14 days (group instilled with beads). 24 hours after the last treatment, the total amikacin and free amikacin were measured as described above. In rats that had received bacteria, an average of approximately 50-70% of the detected amikacin was in the free form, i.e. released from the liposome. In the rats that had not received bacteria approximately 20-25% of the drug was in free form. These data strongly suggest that release of free amikacin from the liposome may be mediated by the presence of $P.$ $aeruginosa$ in vivo.

An in vitro test of release and activity was performed under conditions similar to the pharmacokinetics in the lung, where it has been previously shown that free antibiotic is cleared on the time scale of a few hours. Free amikacin or a liposomal amikacin formulation was incubated with $P.$ $aeruginosa$ PA01 ($\sim 10^8$/mL) in sterile 0.5 mL Slide-A-Lyzer cartridges at varying drug concentrations. Free drug dialyzes out of the cartridges on the time scale of hours under these conditions. After 24 hrs., the samples were withdrawn from the cartridges and plated to measure CFU. In the preliminary experiments free amikacin only slightly reduced the CFU of these samples, while a two log reduction of CFUs was observed for amikacin comprising lipid compositions at the same amikacin concentration (50 µg/mL). These data suggest that amikacin is indeed released in an active form in the presence of bacteria and that the slow release afforded by the formulation makes more effective use of the drug.

The interaction of the liposomal amikacin formulations of the present invention with $P.$ $aeruginosa$ or its virulence factors leads to release of amikacin possibly directing release to the site of infection. When amikacin is released it is active against $P.$ $aeruginosa$, and the slow release in the vicinity of the bactieria may have an advantage over the non-specific distribution and rapid clearance of inhaled free drug.

10.5. Effect of Inhaled Liposomal Drug Formulations on the Function of Alveolar Macrophages The liposomal amikacin formulations of the present invention are in one embodiment a nanoscale (200-300 nm) liposome-encapsulated form of amikacin that is formulated to treat chronic $P.$ $aeruginosa$ infections in cystic fibrosis patients. It is designed for inhalation with sustained release of amikacin in the lung. Because alveolar macrophages are known to avidly take up particles in this size range, the effect of the liposomal formulations on these cells is of particular interest. The basal and stimulated functions of rat alveolar macrophages obtained by lavage were studied with and without administration of liposomal amikacin formulations and compared to various controls.

Aerosols of the liposomal amikacin formulations, amikacin, placebo liposomes and saline were generated with a PARI LC Star nebulizer and inhaled by CD® IGS female rats in a nose-only inhalation chamber. Inhalation therapy was conducted for 4 hr for 14 consecutive days, such that the estimated daily lung dose of total lipid was approximately 12 mg/kg for the liposomal amikacin group and 11 mg/kg for the placebo liposome group. Half the rats were euthanizedon day 15. The remaining rats were euthanized on day 43. Bronchial alveolar lavage fluid (BALF) was collected from each rat and stored at −80° C. for subsequent assay of nitric oxide (as represented by total nitrates) and tumor necrosis factor alpha (TNF-α). The cells from the BALF were collected by centrifugation, counted and cultured in medium with and without lipopolysaccharide (LPS) for 24 hr. The supernatants from these cultures were collected by centrifugation and assayed for nitric oxide and TNF-α. The phagocytic function of BAL macrophages ($(10^6)$/mL) was tested by measuring the overnight uptake of opsonized fluorescent microspheres (0.2 µm, $2 (10^9)$/mL).

Inhalation of the liposomal amikacin formulation, empty liposomes, soluble amikacin, or saline for 14 consecutive days did not produce a significant acute or delayed inflammatory response in the lungs of rats as evident by levels of nitric oxide (nitrates) and TNF-α in BALF which were insignificantly different from controls, although there was an early trend toward higher NO levels in all groups receiving inhalants, including controls. The total recovery of cells was insignificantly different in all groups with an early trend toward more polymorphonuclear leukocytes in all groups receiving inhalants. Rat alveolar macrophages had normal functions after exposure to the aerosols of the above test articles despite the fact that they appeared enlarged on day 15 in groups inhaling liposomes. The concentrations of nitrates and TNF-α detected upon culturing of alveolar macrophages in medium on day 15 or 43 of the study were insignificantly different from controls. The macrophages responded normally when stimulated by LPS, producing substantial concentrations of nitric oxide (20-40 nmol/$10^6$ cells) and TNF-α (5-20 ng/$10^6$ cells). These macrophages also had normal phagocytic functions, as shown by identical uptake of fluorescent beads compared to untreated controls.

Inhalation of the liposomal amikacin formulations for 14 consecutive days did not substantially affect the function of alveolar macrophages in terms of phagocytosis of opsonized beads, production of inflammatory mediators TNF and NO.

11. Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 50 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the antiinfective) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

12. Formulation

The lipid antiinfective formulations of the present invention may comprise an aqueous dispersion of liposomes. The formulation may contain lipid excipients to form the liposomes, and salts/buffers to provide the appropriate osmolarity and pH. The formulation may comprise a pharmaceutical excipient. The pharmaceutical excipient may be a liquid, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient. Suitable excipients include trehalose, raffinose, mannitol, sucrose, leucine, trileucine, and calcium chloride. Examples of other suitable excipients include (1) sugars, such as lactose, and glucose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

EXEMPLIFICATION

Example 1

In-Line Infusion Process

About 20 mg/ml total lipid (DPPC:cholesterol=2:1 by wt) in ethanol and about 75 mg/ml amikacin sulfate (about 50 mg/ml amikacin) in water were mixed together into the reactor vessel by the two-stream in line infusion method. Two solutions were fed into Y-shaped connector at a rate of about 1.0 L/min and about 1.5 L/min, respectively. During the two-stream infusion, water was separately added into the reactor vessel at a similar flow rate (about 1.0 L/min) as the flow rate of lipid solution. The amikacin-lipid suspension infused into the reactor vessel is instantaneously diluted by the continuous feed of water. This additional water helps to seal the membrane by diluting ethanol and it also reduces viscosity of the suspension, consequently reducing the inlet pressure of the diafiltration cartridge. After infusion, the suspension is concentrated by reducing the volume half using diafiltration. The concentrated suspension is washed by diafiltration during a fresh supply of 3.0% NaCl solution. The washed suspension is further concentrated by diafiltration until the desired total amikacin concentration is achieved. The results are given in Table 10.

TABLE 10

| Lot | Washing Temp (° C.) | Total [amikacin] mg/ml | Total [lipid] mg/ml | Lipid/Drug |
|---|---|---|---|---|
| I | RT* | 130.3 | 54.2 | 0.42 |
| II | RT* | 126.0 | 57.0 | 0.45 |
| III | 35 | 130.0 | 60.9 | 0.47 |

*Room temperature (19~23° C.).

Example 2

Encapsulation of Bovine Serum Albumin (BSA) by Coacervation Technique

Figure 12:
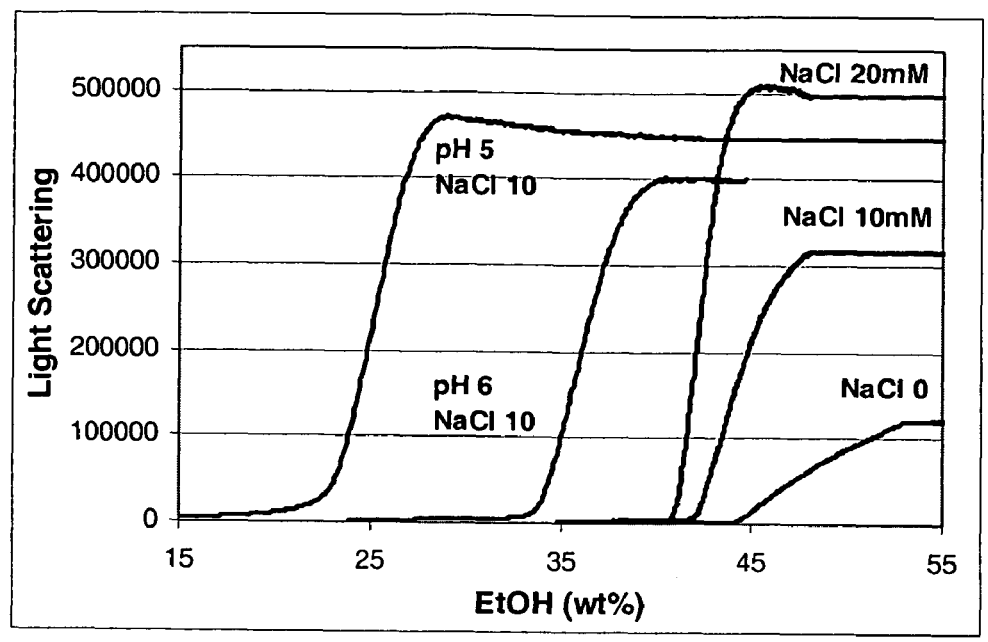
FIG. 12 depicts the effect of ionic strength and pH on ethanol-induced coacervation of BSA. A sample of BSA at 10 mg/mL in an optical cuvette was titrated with a flow of degassed ethanol under constant stirring. Light scattering signal was measured at the right angle at 600 nm wavelength using PTI fluorimeter (Photon Technology International, New Jersey). Temperature was fixed at 25 C.
Figure 13:
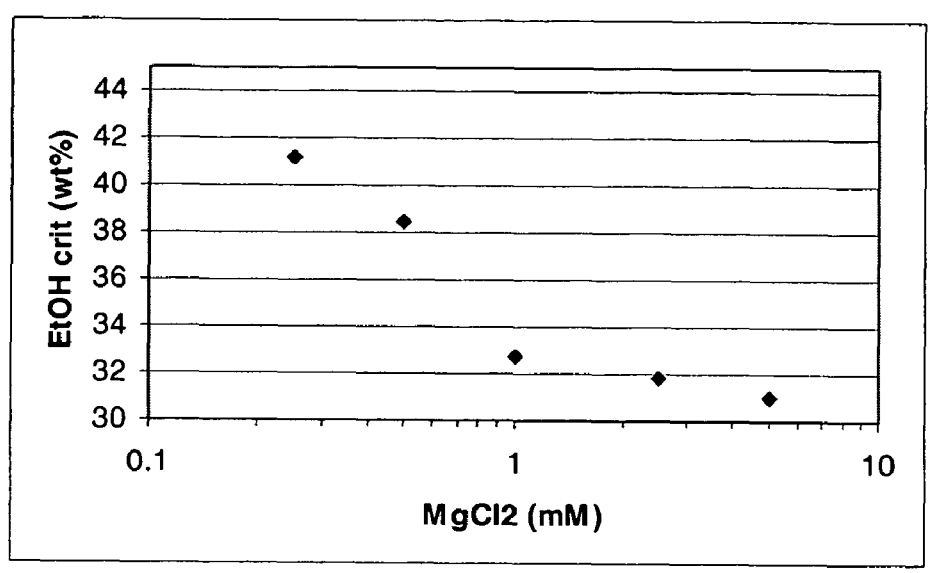
FIG. 13 depicts the effect of $MgCl_2$ on ethanol induced coacervation of BSA. $EtOH_{crit}$ is the concentration of ethanol at the onset of increase in light scattering. BSA 10 mg/mL was dissolved in NaCl 10 mM at pH 7.0.
Figure 14:
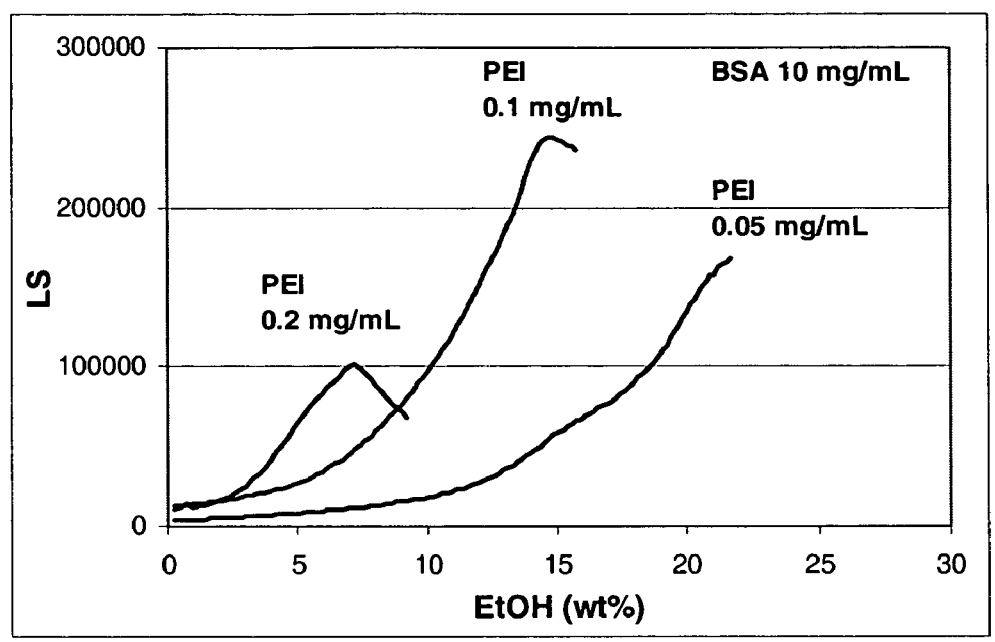
FIG. 14 depicts the effect of low molecular weight (MW 800) polycation Polyethylenimine (PEI) on ethanol induced coacervation of BSA. BSA 10 mg/mL was dissolved in NaCl 10 mM at pH 7.0.

BSA is a protein having isoelectric point pI=4.9. At pH above that point, it can be considered as a colloid with a net negative charge. It has been shown to form complex coacervates with various polyelectrolytes, such as Poly(allylamine hydrochloride), which in turn is affected by the medium ionic strength, pH and temperature. It was found that addition of nonsolvent to albumin (ethanol) can also induce coacervation. When BSA is dissolved in water at pH 7.0, and ethanol concentration added exceeds ~45 wt %, BSA molecules aggregate to form droplets of coacervate phase thus leading to strong increase in light scattering. Adding NaCl (increasing ionic strength) results in less ethanol needed to induce coacervation. Lowering the pH has a similar effect (FIG. 12). Di-valent ions (e.g. $Mg^{2+}$) have an even stronger effect on lowering the critical ethanol concentration required to induce BSA coacervation (FIG. 13). The most drastic effect was found when the low molecular weight polycation PEI was added to the BSA solution (FIG. 14). Thus, 0.05 mg/mL of PEI in molar terms is ~60 µM concentration, which represents only about 1 molecule PEI per 3 molecules of BSA.

To encapsulate BSA into liposomes, a BSA aqueous solution at 10 mg/ml in 20 mM NaCl, pH 5.5 was used. A lipid solution was prepared separately at a concentration of 10 mg/mL and a molar ratio DPPC/DPPG/Cholesterol of 60:5:40 in 95% ethanol. All solutions were preheated to 30° C. The lipid solution (0.4 mL) was added by pipette into a 1 mL BSA solution in a test tube and immediately vortexed to ensure complete mixing. 20 seconds later 0.6 mL of 5% sucrose solution was added and vortexing repeated. To determine BSA encapsulation, 0.8 mL of the resulting liposome suspension was placed on 5-20% sucrose gradient and centrifuged 30 min at 30,000 RPM. The loaded liposomes formed a pellet heavier than 20% sucrose. The pellet was collected and quantitated for lipids and BSA. Lipids were measured by reverse-phase HPLC and BSA was measured by fluorescence (excitation 280 nm, emission 320 nm). It was found that the pellet contained 1.6 mg lipid and 1.3 mg BSA thus giving L/D ratio of 1.2 which is lower than what is normally seen for proteins (for example, see U.S. Pat. No. 6,843,942, where encapsulation of recombinant human superoxide dismutase (rh-SOD) in a DPPC-cholesterol-stearylamine formulation was prepared with a L/D ratio of ~5).

REFERENCES

1. Veldhuizen, R., Nag, K., Orgeig, S. and Possmayer, F., The Role of Lipids in Pulmonary Surfactant, Biochim. Biophys. Acta 1408:90-108 (1998).
2. Hagwood, S., Derrick, M. and Poulain, F., Structure and Properties of Surfactant Protein B, Biochim. Biophys. Acta 1408:150-160 (1998).
3. Johansson, J., Structure and Properties of Surfactant ProteinC, Biochim. Biophys. Acta 1408:161-172 (1998).
4. Ikegami, M. and Jobe, A. H., Surfactant Protein Metabolism in vivo, Biochim. Biophys. Acta 1408:218-225 (1998).
5. Couveur, P., Fattel, E. and Andremont, A., Liposomes and Nanoparticles in the Treatment of Intracellular Bacterial Infections, Pharm. Res. 8:1079-1085 (1991).
6. Gonzales-Rothi, R. J., Casace, J., Straub, L., and Schreier, H., Liposomes and Pulmonary Alveolar Macrophages: Functional and Morphologic Interactions, Exp. Lung Res. 17:685-705 (1991).
7. Swenson, C. E., Pilkiewicz, F. G., and Cynamon, M. H., Liposomal Aminoglycosides and TLC-65 Aids Patient Care 290-296 (Dec., 1991).
8. Costerton, J. W., Stewart, P. S., and Greenberg, E. P., Bacterial Biofilms: A Common Cause of Persistent Infections, Science 284:1318-1322 (1999).
9. Cash, H. A., Woods, D. E., McCullough, W. G., Johanson, J. R., and Bass, J. A., A Rat Model of Chronic Respiratory Infection with *Pseudomonas aeruginosa*, American Review of Respiratory Disease 119:453-459 (1979).
10. Cantin, A. M. and Woods, D. E. Aerosolized Prolastin Suppresses Bacterial Proliferation in a Model of Chronic *Pseudomonas aeruginosa* Lung Infection, Am. J. Respir. Crit. Care Med. 160:1130-1135 (1999).
11. Ramsey, B. W., Dorkin, H. L., Eisenberg, J. D., Gibson, R. L., Harwood, I. R., Kravitz, R. M., Efficacy of Aerosolized Tobramycin in Patients with cystic Fibrosis. New England J. of Med. 328:1740-1746 (1993).
12. Mendelman, P. M., Smith, A. L., Levy, J., Weber, A., Ramsey, B., Davis, R. L., Aminoglycoside Penetration, Inactivation, and Efficacy in Cystic Fibrosis Sputum, American Review of Respiratory Disease 132:761-765 (1985).
13. Price, K. E., DeFuria, M. D., Pursiano, T. A. Amikacin, an aminoglycoside with marked activity against antibiotic-resistant clinical isolates. J Infect Dis 134:S249261 (1976).
14. Damaso, D., Moreno-Lopez, M., Martinez-Beltran, J., Garcia-Iglesias, M. C. Susceptibility of current clinical isolates of *Pseudomonas aeruginosa* and enteric gram-negative bacilli to Amikacin and other aminoglycoside antibiotics. J Infect Dis 134:S394-90 (1976).
15. Pile, J. C., Malone, J. D., Eitzen, E. M., Friedlander, A. M., Anthrax as a potential biological warfare agent. Arch. Intern. Med. 158:429-434 (1998).
16. Gleiser, C. A., Berdjis, C. C., Hartman, H. A., & Glouchenour, W. S., Pathology of experimental respiratory anthrax in Macaca mulatta. Brit. J. Exp. Path., 44:416-426 (1968).

INCORPORATION BY REFERENCE

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

EQUIVALENTS

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of delivering a liposomal aminoglycoside formulation at a rate of 10 to 25 mg/min of aminoglycoside comprising nebulizing the liposomal aminoglycoside formulation, wherein the liposomal aminoglycoside formulation comprises a lipid bilayer and an aminoglycoside encapsulated therein, and wherein the formulation has a lipid to aminoglycoside (L/D) weight ratio ranging from 0.40:1 to 0.49:1.

2. The method of claim 1, wherein the amount of aminoglycoside encapsulated in the liposome after the nebulization is greater than 45% of the amount of aminoglycoside encapsulated before the nebulization.

3. The method of claim 1, wherein the lipid is a mixture of a phospholipid and a sterol.

4. The method of claim 3, wherein the phospholipid is dipalmitoylphosphatidylcholine (DPPC) and the sterol is cholesterol.

5. The method of claim 4, wherein the DPPC:cholesterol ratio is 2:1 by weight.

6. The method of claim 1, wherein the aminoglycoside is amikacin.

7. The method of claim 1, wherein the aminoglycoside is tobramycin.

8. The method of claim 1, wherein the aminoglycoside is gentamicin.

9. A method of treating a patient for a pulmonary infection comprising administering to the patient in need thereof a therapeutically effective amount of a liposomal aminoglycoside formulation, wherein the liposomal aminoglycoside formulation comprises a lipid bilayer and an aminoglycoside encapsulated therein, and wherein the formulation has a lipid to aminoglycoside (L/D) weight ratio ranging from 0.40:1 to 0.49:1.

10. The method of claim 9, wherein the aminoglycoside is amikacin.

11. The method of claim 9, wherein the aminoglycoside is tobramycin.

12. The method of claim 9, wherein the aminoglycoside is gentamicin.

13. The method of claim 9, wherein the pulmonary infection is a pseudomonas, *P. aeruginosa, P. paucimobilis, P. putida, P. fluorescens*, and *P. acidovorans*, staphylococcal, Methicillinresistant *Staphylococcus aureus* (MRSA), streptococcal, *Streptococcus pneumoniae, Escherichia coli, Klebsiella, Enterobacter, Serratia, Haemophilus, Yersinia pesos, Burkholderia pseudomallei, B. cepacia, B. gladioli, B. multivorans, B. vietnamiensis, Mycobacterium tuberculosis, M. avium* complex (MAC), *M. avium, M. intracellulare, M. kansasii, M. xenopi, M. marinum, M. ulcerans, M. fortuitum* complex, *M. fortuitum*, or *M. chelonei* infection.

14. The method of claim 9, wherein the patient has cystic fibrosis.

15. The method of claim 10, wherein the patient has cystic fibrosis.

16. The method of claim 11, wherein the patient has cystic fibrosis.

17. The method of claim 12, wherein the patient has cystic fibrosis.

18. The method of claim 1, using a nebulizer compressor pressure of 20 to 40 psi.

* * * * *